US006454716B1

United States Patent
Zumeris

(10) Patent No.: US 6,454,716 B1
(45) Date of Patent: Sep. 24, 2002

(54) SYSTEM AND METHOD FOR DETECTION OF FETAL HEARTBEAT

(75) Inventor: Jona Zumeris, Nesher (IL)

(73) Assignee: P.M.G. Medica Ltd., Nesher (IL)

( * ) Notice: Subject to any disclaimer, the term of this patent is extended or adjusted under 35 U.S.C. 154(b) by 0 days.

(21) Appl. No.: 09/577,385

(22) Filed: May 23, 2000

(51) Int. Cl.⁷ ............................................. A61B 8/02
(52) U.S. Cl. ..................................................... 600/453
(58) Field of Search ........................... 600/437, 438, 600/453–456, 459

(56) References Cited

U.S. PATENT DOCUMENTS

| | | | |
|---|---|---|---|
| 3,561,430 A | * 2/1971 | Filler, Jr. ..................... | 600/453 |
| 3,859,984 A | 1/1975 | Langley | |
| 4,092,867 A | * 6/1978 | Matzuk ....................... | 600/443 |
| 4,413,629 A | 11/1983 | Durley, III | |
| 4,503,861 A | 3/1985 | Entrekin | |
| 4,646,754 A | * 3/1987 | Seale .......................... | 600/587 |
| 4,757,821 A | 7/1988 | Snyder | |
| 4,771,792 A | * 9/1988 | Seale .......................... | 600/587 |
| 4,966,152 A | 10/1990 | Gang et al. | |
| 5,471,988 A | * 12/1995 | Fujio et al. ................. | 600/439 |
| 5,505,088 A | * 4/1996 | Chandraratna et al. ..... | 600/461 |
| 5,509,416 A | 4/1996 | Wilmott | |
| 5,551,437 A | 9/1996 | Lotscher | |
| 5,605,154 A | * 2/1997 | Ries et al. ................... | 600/444 |
| 5,795,300 A | 8/1998 | Bryars | |
| 5,817,035 A | 10/1998 | Sullivan | |
| 5,823,963 A | * 10/1998 | Takeuchi ..................... | 600/443 |
| 5,844,140 A | * 12/1998 | Seale .......................... | 73/633 |
| 5,904,654 A | 5/1999 | Wohltmann et al. | |
| 6,068,597 A | * 5/2000 | Lin ............................. | 600/459 |
| 6,110,121 A | * 8/2000 | Lenker ........................ | 600/463 |

* cited by examiner

Primary Examiner—Francis J. Jaworski
(74) Attorney, Agent, or Firm—Eitan, Pearl, Latzer & Cohen-Zedek

(57) ABSTRACT

The present invention provides a device and method for monitoring and detecting a fetal heartbeat that can be employed by ordinary people with minimal, if any, training, such as expectant mothers. The device can monitor and detect a fetal heartbeat with minimal positioning along the female body at the pregnant portion (the womb) as the device is configured to transmit and receive energy waves at wide angles. The device is economical and is preferably designed for domestic use, outside of the hospital or clinical setting. Specifically, the invention is based on a unique configuration of piezoelectric elements in cooperative configuration with a series of oscillators that is able to transmit and receive ultrasonic waves simultaneously The configuration allows for an optimal scanning range at an unlimited number of angles.

39 Claims, 22 Drawing Sheets

SYSTEM AND METHOD FOR DETECTION OF FETAL HEARTBEAT

FIELD OF THE INVENTION

The present invention relates to heart rate detection and in particular to devices for monitoring and detection of fetal heartbeat.

BACKGROUND OF THE INVENTION

Detection of fetal heartbeat has been an important indicator of the health of a fetus and is routinely performed by health professionals. Additionally, the expectant mother and others around her are also interested in detecting and hearing this heartbeat.

Devices used for fetal heartbeat detection and monitoring by health professionals are such that their operation typically requires substantial medical training For example, operation of these devices involves manually moving the head containing the transmitter and receiver until the heartbeat is detected. This is because these devices typically employ ultrasonic waves that are transmitted from and received by the device in a "straight line" manner.

Also, these devices may be of a size so as to be limited to hospital or other clinical settings. Moreover, these devices are expensive and not suitable for home or domestic use by ordinary individuals.

Devices suitable for home or domestic usage are available, for example a portable ultrasonic doppler system described in U.S. Pat. No. 4,413,629, a fetal heart detector described in U.S. Pat. No. 4,413,629, a transducer for extra-uterine monitoring of fetal heart rate described in U.S. Pat. No. 4,966,152 and a Biophysical Fetal Monitor as described in U.S. Pat. No. 5,817,035. However, these devices are expensive and like the professional devices require the user to manually move portions of the device to locate the heartbeat, as these devices also operate in the fetal straight-line manner. Alternatively, a multiple array of sensors is used to achieve adequate coverage in order to locate the fetal heart.

SUMMARY OF THE INVENTION

The present invention provides a device and methods for monitoring and detecting a fetal heartbeat that can be employed by ordinary people with minimal, if any, training. The device can monitor and detect a fetal heartbeat with minimal positioning along the female body at the pregnant portion (the womb) as the device is configured to transmit and receive energy when at wide angles. The device is economical and is preferably designed for domestic use, outside of the hospital or clinical setting.

The present invention relates to an apparatus for scanning and receiving energy waves having at least one piezoelectric transmitter, at least one piezoelectric receiver, and at least one support member for the transmitter and receiver. The support member is operatively coupled to at least one piezoelectric transmitter and at least one piezoelectric receiver for oscillating synchronously over a predetermined range of voltages and frequencies and transceiving energy waves over a predetermined angular range.

In a further embodiment the present invention also includes at least one oscillator in communication with the support member, for vibrating the support member. Typically, the oscillator is configured for operation based on a sinusoidal wave input or based on a standing wave input. However, other wave types are possible as well.

In a further embodiment of the present invention, the apparatus also has at least one oscillator in communication with the piezoelectric transmitter, for vibrating the piezoelectric transmitter. Typically, the oscillator is configured for operation based on a sinusoidal wave input or on a standing wave input. although other wave types are possible as well, In a further embodiment of the present invention, the apparatus as described hereinabove further includes at least one activatable vibrating element in communication with the support member, whereby the element is configured for communication with the piezoelectric transmitter and piezoelectric receiver to achieve variability in scanning. The activatable vibrating element may be a piezoelectric disc, plate or torsional element or any other configuration. Typically, the support member comprises piezo-ceramic material.

The piezoelectric transmitter and piezoelectric receiver may be configured in various shapes to achieve variability in scanning. Further, the piezoelectric transmitter and piezoelectric receiver may comprise piezo-ceramic material.

In a further embodiment of the present invention, the piezoelectric transmitter and piezoelectric receiver may be configured to vibrate in a perpendicular direction with respect to the support member.

In one embodiment of the present invention, the apparatus may additionally include one or more filter layers operatively coupled to the support member. This filter layer may have a thickness of approximately ¼ the wavelength of the energy waves transmitted by the piezoelectric transmitter.

The at least one piezoelectric transmitter may, include one piezoelectric transmitter or multiple piezoelectric transmitter elements. Similarly, the at least one piezoelectric receiver may include one piezoelectric receiver or multiple piezoelectric receiver elements. Further, the at least one support member may comprise individually activatable sections.

The present invention further relates to a system for detecting a fetal heartbeat having at least one piezoelectric transmitter, at least one piezoelectric receiver, at least one support member for the transmitter and receiver, and an amplifier unit. The support member is operatively coupled to at least one piezoelectric transmitter and at least one piezoelectric receiver for oscillating synchronously over a predetermined range of voltages and frequencies and transceiving energy waves over a predetermined angular range. The amplifier unit in communication with the piezoelectric transmitter is configured for converting the received energy waves into an output signal.

In a further embodiment the present invention also comprises at least one oscillator in communication with the support member, for vibrating the support member. Typically, the oscillator is configured for operation based on a sinusoidal wave input or based on a standing wave input. However, other wave types are possible as well.

In a further embodiment of the present invention, the system also has at least one oscillator in communication with the piezoelectric transmitter, for vibrating the piezoelectric transmitter. Typically, the oscillator is configured for operation based on a sinusoidal wave input or on a standing wave input, although other wave types are possible as well.

In a further embodiment of the present invention, the system as described hereinabove further includes at least one activatable vibrating element in communication with the support member, whereby the element is configured for communication with the piezoelectric transmitter and piezoelectric receiver to achieve variability in scanning The activatable vibrating element may be a piezoelectric disc, plate or torsional element, or any other configuration. Typically, the support member comprises piezo-ceramic material.

The piezoelectric transmitter and piezoelectric receiver may be configured in various shapes to achieve variability in scanning. Further, the piezoelectric transmitter and piezoelectric receiver may comprise piezo-ceramic material.

In one embodiment of the present invention, the output signal is in the form of audio output via speaker. In another embodiment of the present invention, the output signal is in the form of digital display via counter.

In a further embodiment of the present invention, the piezoelectric transmitter and piezoelectric receiver may be configured to vibrate in a perpendicular direction with respect to the support member.

In one embodiment of the present invention, the system may additionally include one or more filter layers operatively coupled to the support member. This filter layer may have a thickness of approximately ¼ the wavelength of the energy waves transmitted by the piezoelectric transmitter.

The at least one piezoelectric transmitter may include one piezoelectric transmitter or multiple piezoelectric transmitter elements. Similarly, the at least one piezoelectric receiver may include one piezoelectric receiver or multiple piezoelectric receiver elements. Further, the at least one support member may comprise individually activatable sections.

The present invention further relates to a method for detecting a fetal heartbeat including the steps of providing at least one piezoelectric transmitter, at least one piezoelectric receiver and at least one support member for the piezoelectric transmitter and piezoelectric receiver, energizing the support member and the piezoelectric transmitter to create a scanning range over a predetermined arc, and transceiving signals over the predetermined arc so as receipt provides signals corresponding to a fetal heartbeat. The support member is operatively coupled to the piezoelectric transmitter and the piezoelectric receiver for oscillating synchronously over a predetermined range of voltages and frequencies and transceiving energy waves over a predetermined angular range.

In a further embodiment of the present invention, the method further includes the step of varying the scanning sequence. This may be accomplished by varying the voltage input, by varying the frequency input, or by varying the wave input. The energizing step may be accomplished by inputting a continuous signal or a pulsed signal. Further, the energizing step may be accomplished by inputting several signals for progressive wave scanning.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
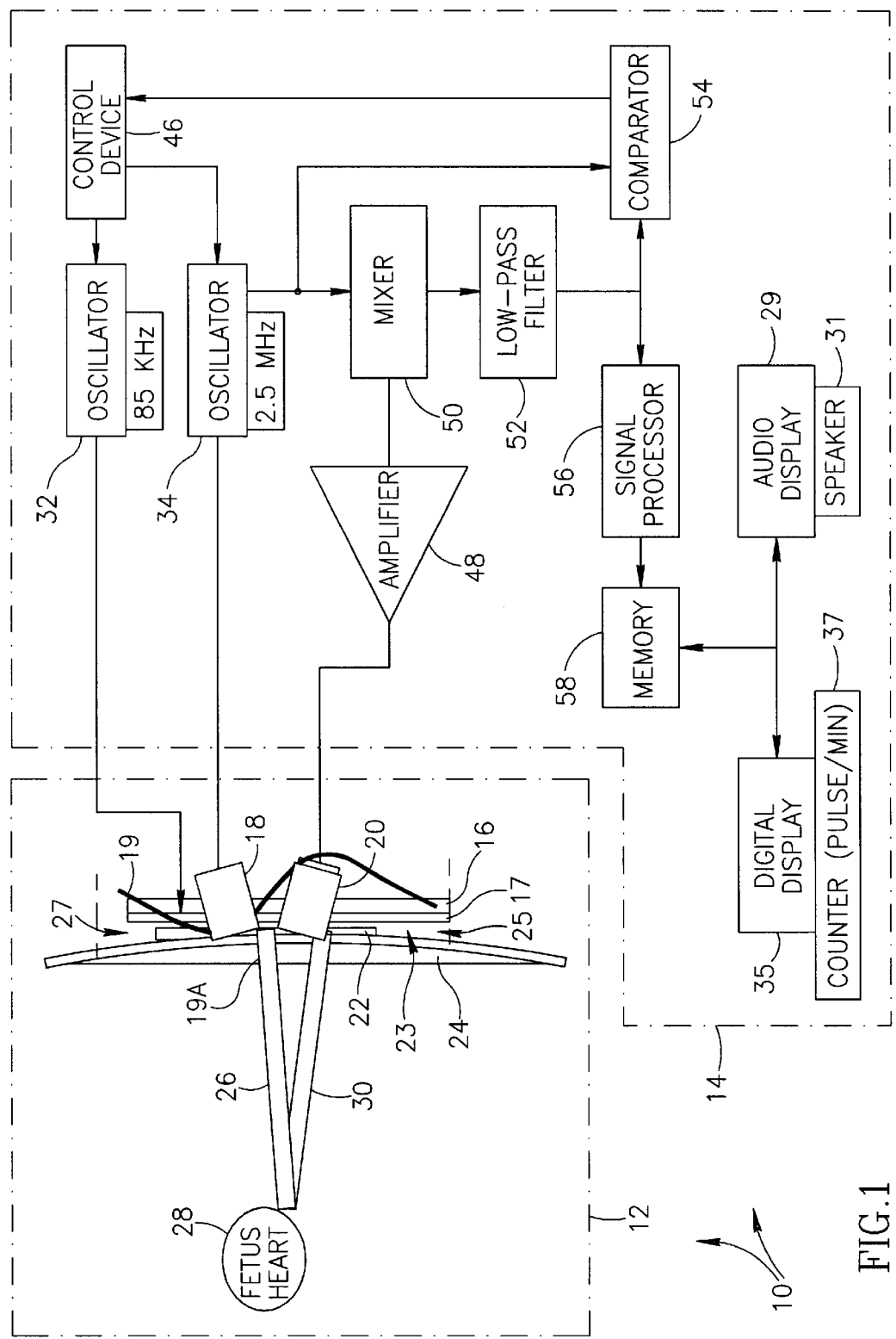
FIG. 1 is a schematic illustration including a block diagram illustration of the entire system.

Reference is now made to FIG. 1, which illustrates an embodiment of the invention, a fetal heartbeat detection system 10. System 10 comprises a scanning system 12 and a signal control and processing system 14. Scanning system 12 functions to transmit energy waves to a scanned area containing the fetal heart and receive reflected waves corresponding to the fetal heartbeat. Processing system 14 signals scanning system 12 to produce energy waves and processes signals corresponding to the received energy waves into audible sounds corresponding to the fetal heartbeat. This allows the mother to listen to her baby's heart.

Scanning system 12 has a piezo-ceramic plate 16 to which are attached an energy wave transmitter 18 and an energy wave receiver 20. The transmitter 18 is made of piezoelectric material and will oscillate in response to an electrical input. The receiver 20 is also made of piezoelectric material and will transmit an electrical signal based on detected mechanical waves. The transmitter 18 and the receiver 20 are, for example, attached using an adhesive which matches the acoustic properties of the transmitter 18 and the receiver 20 to the piezo-ceramic plate 16. This adhesive does not provide acoustic impedance so there is no energy loss or damping from the adhesive. The embodiment shown illustrates transmitter 18 and receiver 20 separately configured for continuous doppler ultrasound scanning where receiver 20 is oriented to receive returning waves from transmitter 18, that typically diverge by an angle of 1–3 degrees, which continuously transmits as it scans across the mother's abdomen. Other configurations suitable for pulsed ultrasound and a canning array are shown and described hereinbelow with reference to FIGS. 6A–6C and 7A–7D.

The Piezo-Ceramic plate 16 is made of a piezo-ceramic material such as Plumbum Zirconium Titanium (PZT), for example PZT-4 or PZT-5 (Morgan Matroc. Inc., Bedford, Ohio) or comparable materials from other suppliers. The material vibrates at a frequency of 30–100 kilohertz (kHz) (in the non-audible range for people), which is the natural frequency of piezo-plate 16, when an electric current is applied. The mode of vibration used is the second mode according to beam theory, as described hereinbelow. The mode of vibration is shown schematically in FIG. 1 and designated 19, although the orientation of transmitter 18 and receiver 20 as shown is not illustrated in relation to the orientation of the second mode representation, (transmitter 18 and receiver 20 are actually placed to be always within the flat section 19a of the representation 19, thus scanning synchronously). A silver electrode (not shown) attached to a backing material 17 of, for example, brass of thickness 50–200 micrometers conveys the necessary current to the piezo-electric plate 16. Backing material 17 also adds strength to the piezo-electric plate 16, enabling the plate 16 to be approximately 0.2 mm thick, which in turn enables a low voltage of approximately 2–15 V to be used to obtain the necessary vibrations. Backing material 17 is also covered with isolating material, for example, plastic, of approximate thickness 0.02 mm (not shown). The voltage used decreases the chances of electric shock to the mother.

Transmitter 18 and receiver 20 are also made of piezo-ceramic material such as PZT-4 or PZT-8 (Morgan Matroc, Inc., Bedford, Ohio) and typically vibrate at a natural frequency of approximately 2.5 megahertz (MHz) for the transmitter 18 and approximately 2.4–2.6 (MHz) for the receiver 20, when operating in a continuous doppler mode as described further hereinbelow. The frequency of vibration of the receiver 20 is approximately the frequency of received ultrasound waves. Receiver 18 and transmitter 20 are connected to an electric current in a similar way to the piezo-ceramic plate 16, and vibrate in the "thickness mode of vibration" i.e. perpendicular to the surface of the piezo-ceramic plate 16. The matching layer 22 is made of a material, such as plastic or indeed any other non-sound absorbent material and its function is to be placed in contact with the mother's skin (at the abdomen 24) when scanning takes place in order to form an interface between the transmitter 18 and the receiver 20. The width of the matching layer 22 (approx. 0.4 mm) is 0.25 of the wavelength of the transmitted energy waves in order to 'match' the transmitter 18 to the mother's skin and prevent the transmitted energy waves being damped out. The width of the transmitter 18 (approx. 0 8 mm) (i.e., the width of the piezo-ceramic element of the transmitter 18) is 0.5 times the wavelength of the transmitted energy waves. The matching layer 22 also prevents the mother receiving a shock from the piezo-ceramic plate 16, the transmitter 18 and the receiver 20.

The scanning system 12 may be divided for the purposes of designation into two parts. The first part is a scanner 23 comprising piezo-ceramic plate 16 and matching layer 22 and the second part is a transducer or probe 25. The probe 25 comprises the transmitter 18 and receiver 20. The scanner 23 and probe 25 together form a scanning probe 27.

The system 10 locates and monitors the fetal heartbeat by the placement of the scanning system 12 in the vicinity of the fetus on the mother's abdomen 24. The scanner then locates the heartbeat by scanning the area of the uterus within the abdomen 24 over a wide angle with doppler ultrasound using the transmitter 18. The wide angle scanning is achieved by applying a harmonic or pulse signal, for example a sinusoidal wave of the natural frequency of the scanning probe 27 to the piezo-ceramic plate 16 to cause scanning to occur, until the fetal heartbeat is detected by the receiver 20. The piezo-ceramic plate 16 vibrates at its natural frequency of 30–100 kHz, which is in the non-audible range for humans, as described hereinabove. Thus, the transmitter 18 and the receiver 20 sweep a synchronized path by virtue of their attachment to the piezo ceramic plate 16 via matching layer 22. The transmitted energy (ultrasound) waves 26 are reflected when they encounter the fetus heart 28 to produce the deflected energy (ultrasound) wave 30 which is received by the receiver 20. The scanning typically takes place at a frequency of 85 kHz, in the present application, driven by a current provided by an oscillator 32 within a processing system 14. A second oscillator 34 provides an alternating current that is supplied to the transmitter 18 at a frequency of, for example, 2.5 MHz, in the present application. This causes the production of the ultrasonic energy waves 26 towards the fetal heart 28. The movement of the fetal heart 28 is detected by the processing system 14 by detecting the doppler shift in frequency as is described in greater detail hereinbelow. This shift may be outputted as an audio output via an audio output device 29 and speaker 31 This enables the mother to reassuringly hear her baby's heartbeat. The doppler shift may also be outputted digitally via a digital display 35 and counter 37.

Figure 2A:
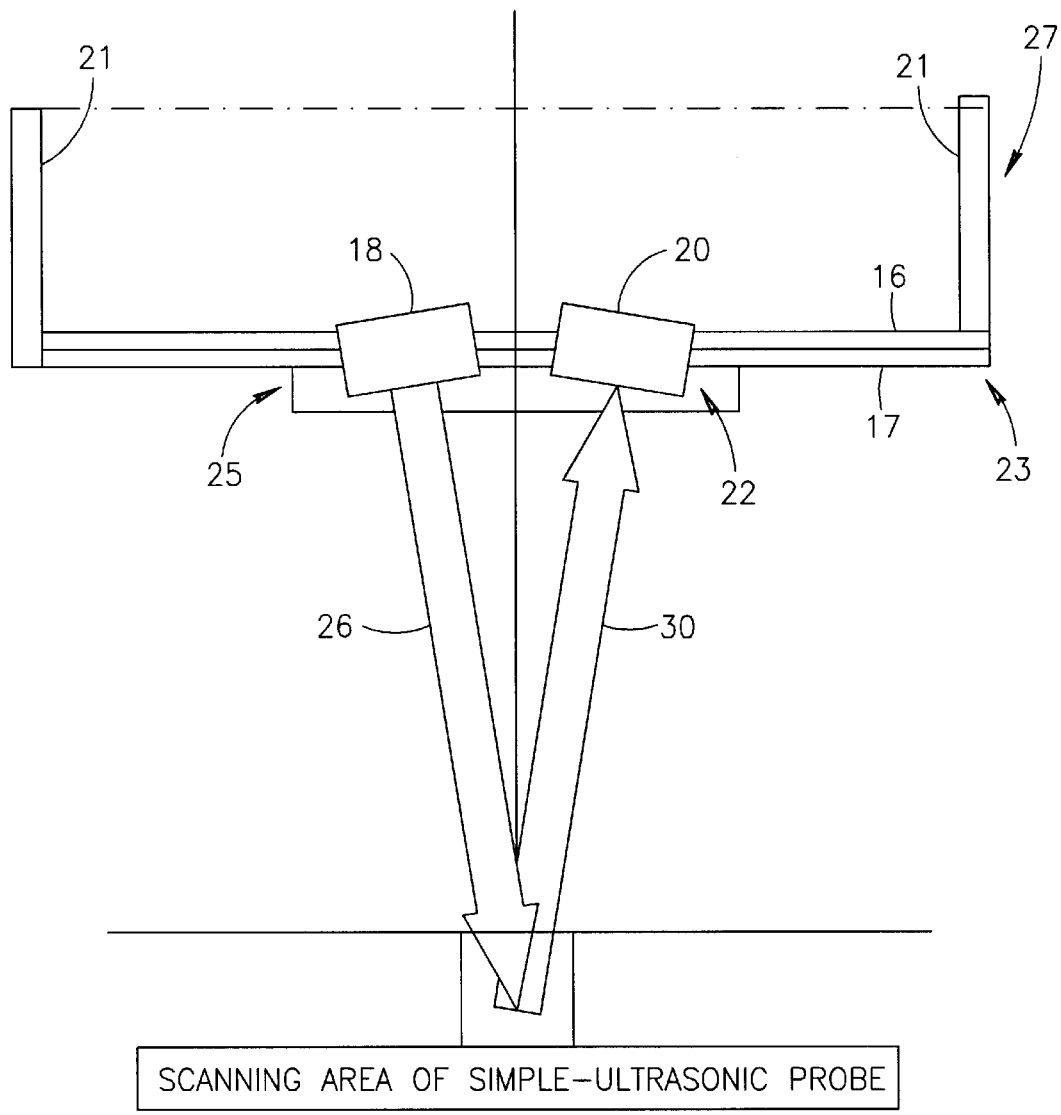
FIGS. 2A–2C illustrate the operation of the scanning system during continuous doppler mode.
Figure 2B:
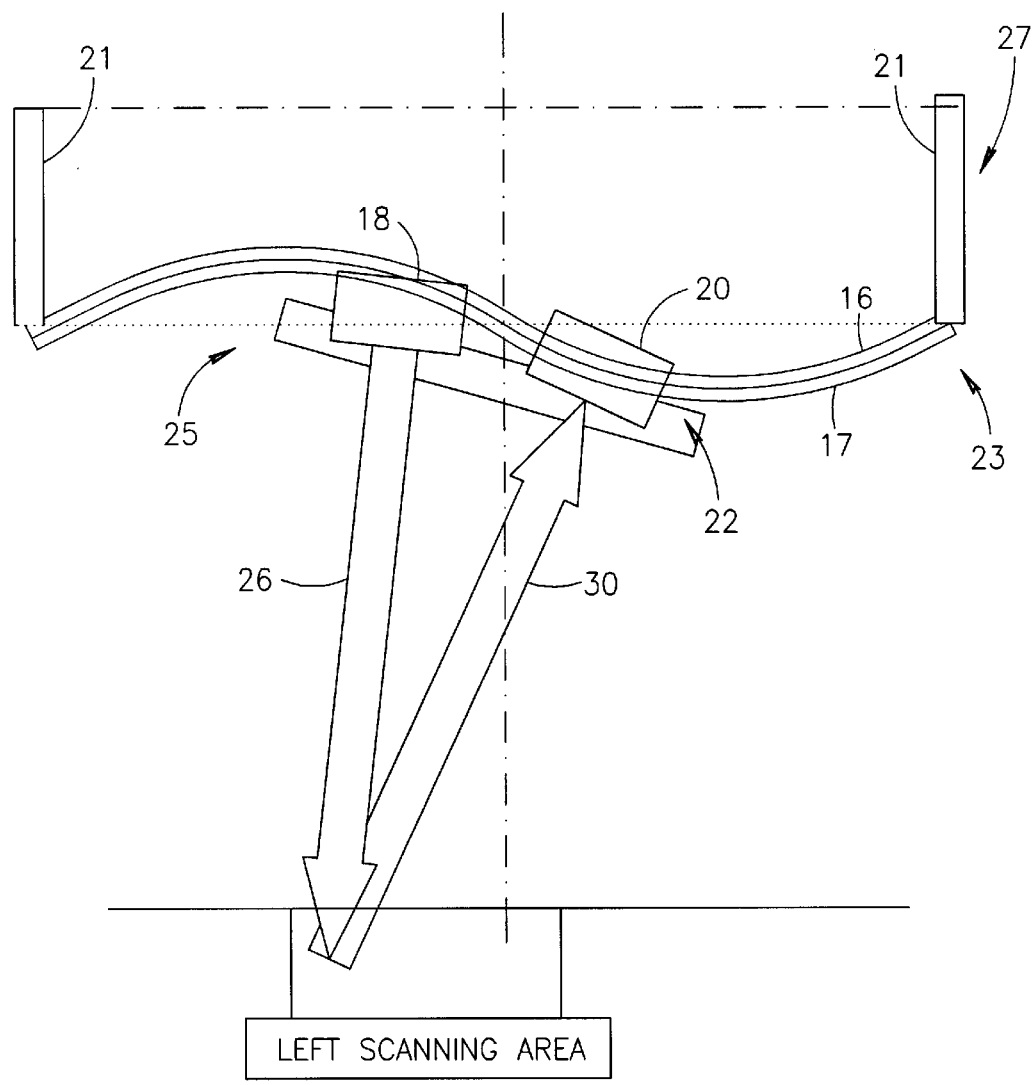
Figure 2C:
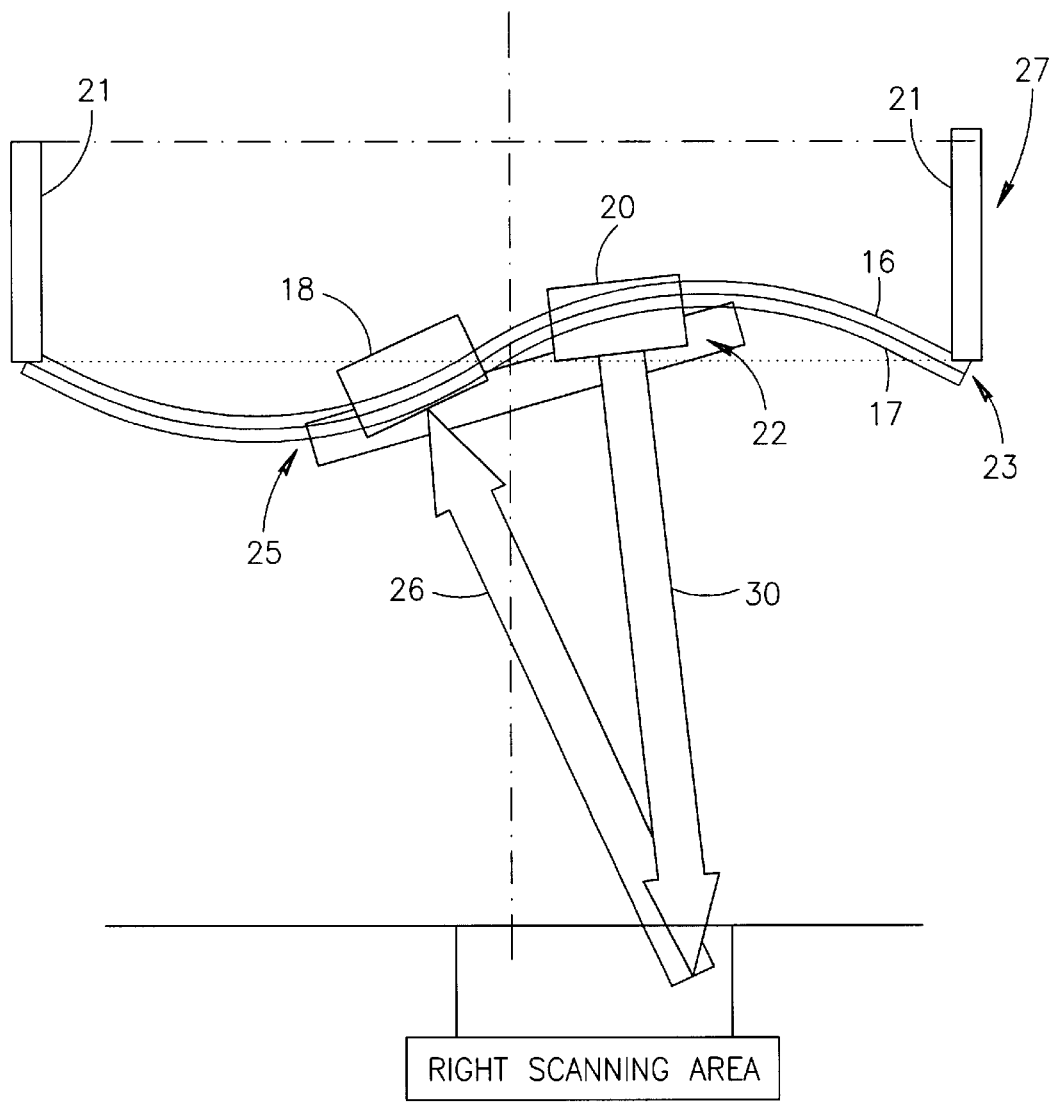

Reference is now made to FIGS. 2A, 2B and 2C, which illustrate the operation of scanning system 12 when configured for a continuous doppler mode of operation. Thus, the transmitter 18 and receiver 20 are separate units allowing the transmitter 18 to transmit continuously and the receiver 20 to be capable of receiving continuously. FIGS. 2A, 2B and 2C illustrate when the transmitter 18 and receiver 20 are respectively oriented to scan to the central position (zero scan angle, 1–3 degree separation between transmitter 18 and receiver 20, see above and further hereinbelow), when they are oriented to scan to the leftmost position, and when they are oriented to scan to the rightmost position. Similar items to previous figures have similar numerals and will not be described further.

A harmonic wave of a frequency of approximately 85 kHz is applied to the piezo-ceramic plate 16 which is anchored at each end to a plastic casing 21. The wave applied can be of running or standing types, and can be applied in bursts. For exemplary purposes, a sinusoidal wave is described. The frequency applied to the piezo-ceramic plate 16 is designed to vibrate the plate 16 in, for example, its second mode of vibration (taking the piezo-ceramic plate 16 as a beam anchored at two points 21). The second mode is chosen because the flat area 19a of the graphical representation 19 (FIG. 1) readily accommodates the transmitter 18 and receiver 20 so that they scan together. This produces a range of angular orientations of transmitted ultrasound energy beams 26 from the scanner 23 between the leftmost extreme of FIG. 2B and the rightmost extreme of FIG. 2C, due to the scanning effect of the vibrating piezoelectric plate 16. The range from the central position, as shown in FIG. 2A is typically 10 degrees on either side, providing a scanning arc, over a 20 degree range, but may be as high as 20 degrees on either side, providing a scanning arc over a 40 degree range.

Figure 2D:
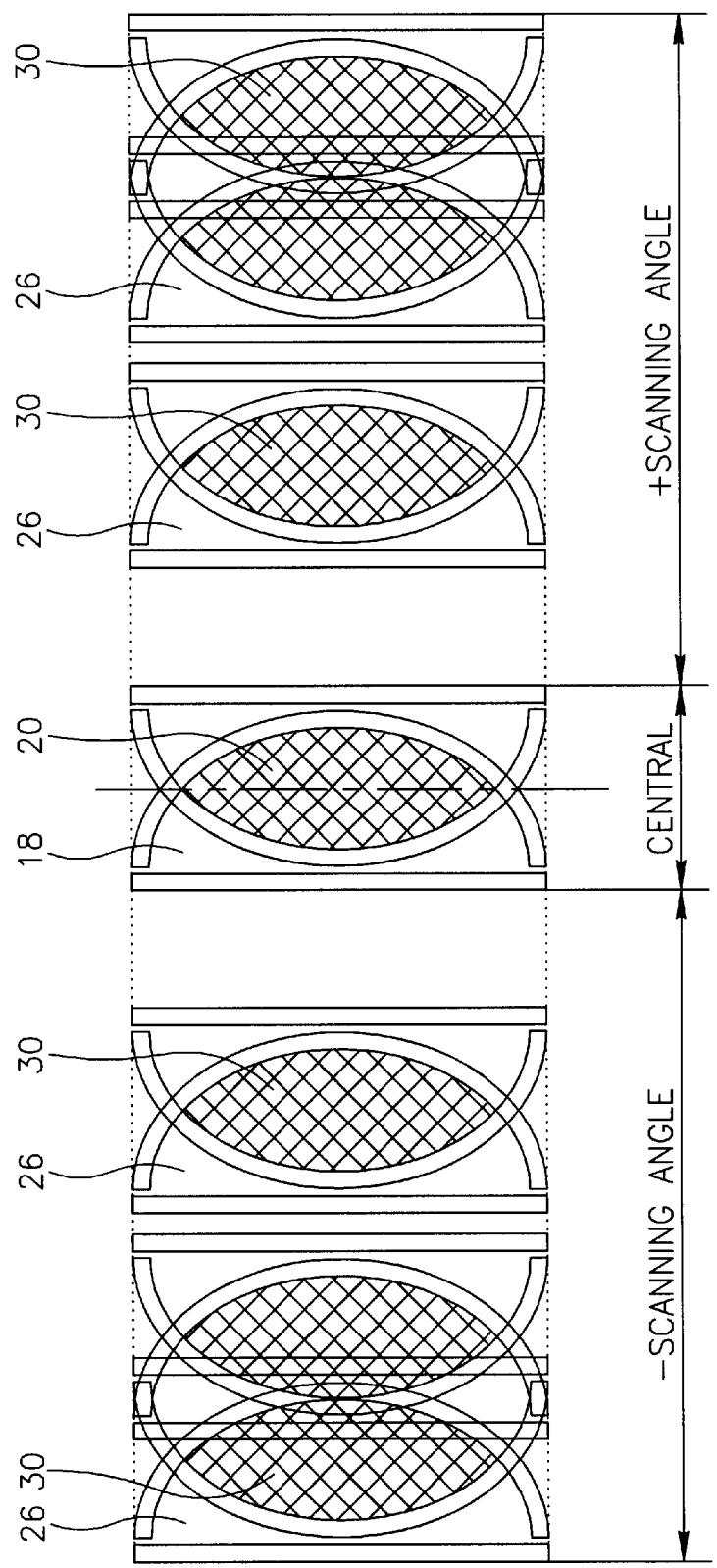
FIG. 2D is an illustration of the scanning pattern on the mother's abdomen.

It should be noted that there is a fixed angular separation of 1–3 degrees between the transmitter 18 and receiver 20 so that the receiver 20 is in the path of the returning transmitted waves 30. When the sinusoidal wave is a peak, the scanner is moving to or from the middle (FIG. 2A) to the leftmost deflected position (FIG. 2B). When the sinusoidal wave is a trough, the scanner is moving to or from the middle (FIG. 2A) to the rightmost deflected position (FIG. 2C) with decreasing degrees of deflections in between as the sine wave varies in amplitude FIG. 2D is a view of the scanning pattern on the mothers abdomen 24, utilizing a sinusoidal wave, showing the semicircular pattern of transmitted beams 26 on the mother's skin and the position from which beams 30 are received by the receiver 20. The semi-circular shape of the scanning pattern is due to the exemplary semi-circular shape of transmitter 18 and receiver 20 as described hereinbelow. Other shapes could also be used. At the zero points of the sinusoidal wave, the scanning probe 27 will be aimed at the central position, as shown in FIGS. 2A and 2D. Thus, in all orientations, the transmitter 18 transmits energy waves 26 at an angle to the skin of the mother and the receiver 20, synchronized with the transmitter 18 by being mounted on the piezo-ceramic plate 16 at the fixed relative angle described hereinabove, is oriented to receive any returning waves 30. Thus, the doppler shift due to the movement of the heart may be detected. Of course, returning waves are only produced when the fetal heart is located in the path of the transmission.

Reference is now further made to FIG. 1, which illustrates the operation the signal control and processing system 14. A control device 46, which may be activated by an untrained user, is utilized to initiate oscillators 32 and 34 to produce signals in the range of frequencies of 20–100 kHz (non-audible) and 2.5 MHz (non-audible) respectively. The oscillators 32 and 34 cause the transmitter 18 to transmit energy waves, and the piezo-ceramic plate 16 to oscillate, thus produce the scanning sequence as described hereinabove. When the fetal heart 28 encounters a transmitted energy wave 26, the receiver 20 receives the reflected received wave 30 with attendant doppler shift. This wave is inputted to an amplifier 48 for amplification, mixed with the output of the oscillator 34 in a mixer 50, passed through a low-pass filter 52 and compared with the frequency transmitted by the oscillator 34 by a comparator 54 to ascertain the doppler shift which is a function of the movement of fetal heart 28 The output from the comparator 54 is fed into a signal processor 56 and stored in memory 58 from where it may be outputted as audio output 29 via a speaker 31 thus enabling the mother to listen to the fetus' heart 28, or as a digital display 35 via a counter 37.

Figure 3A:
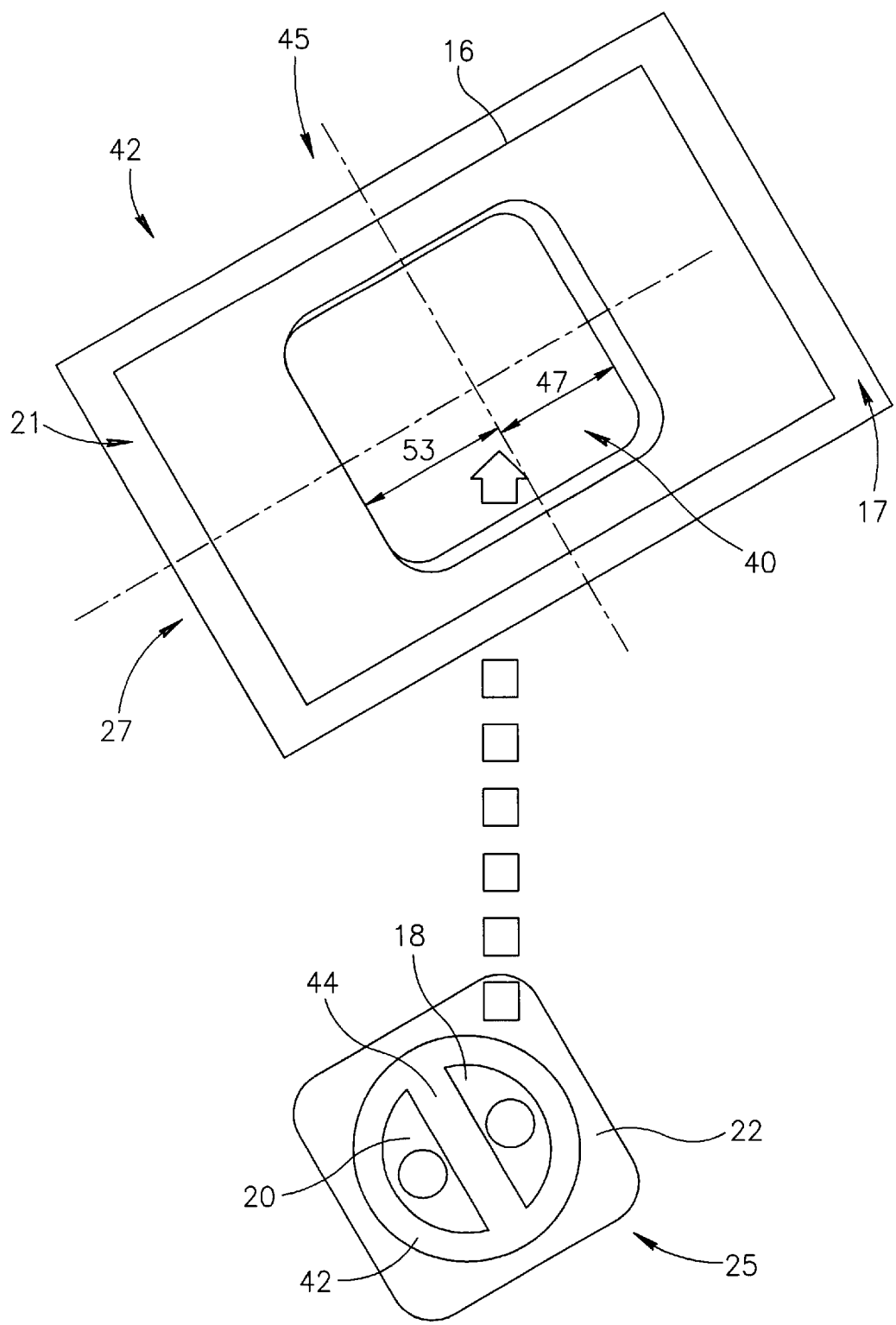
FIGS. 3A–3C are illustrations of the component parts of the scanning probe.
Figure 3B:
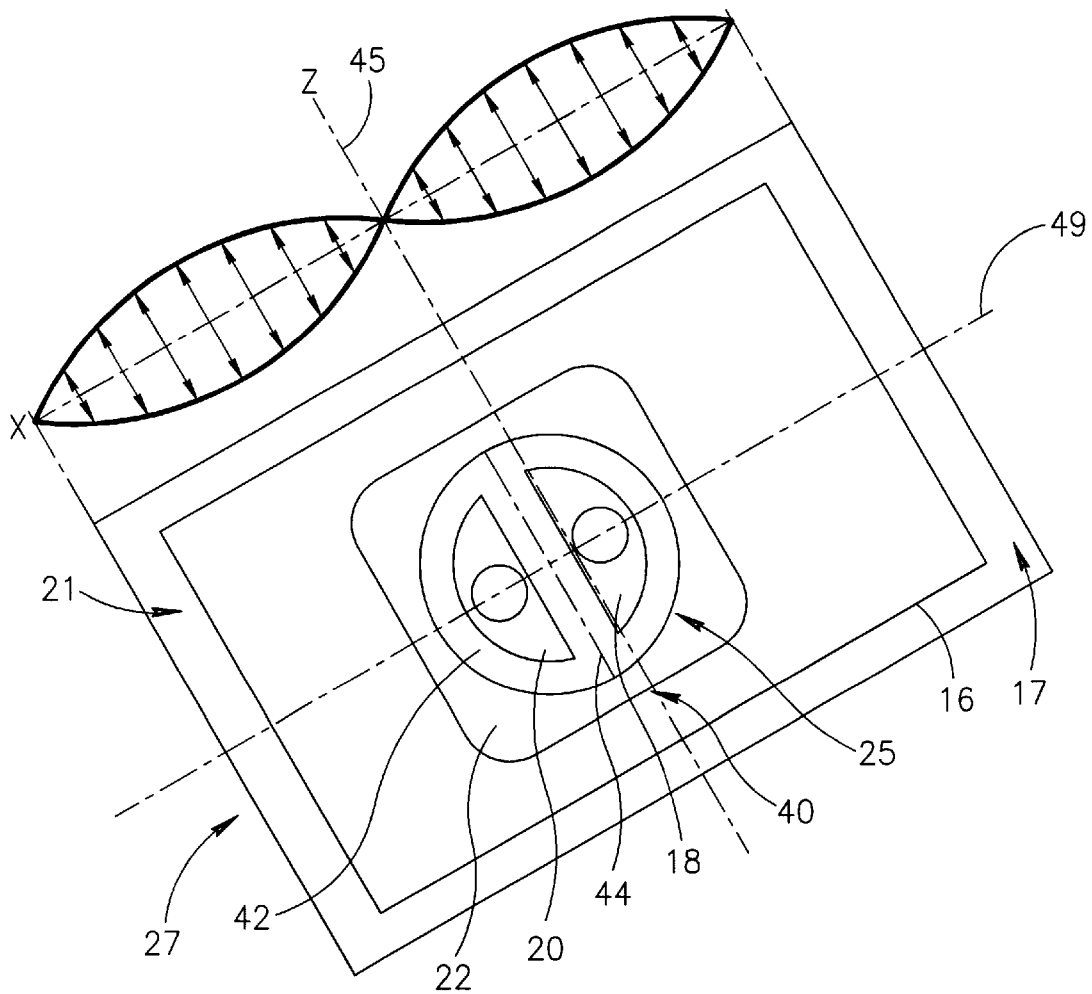
Figure 3C:
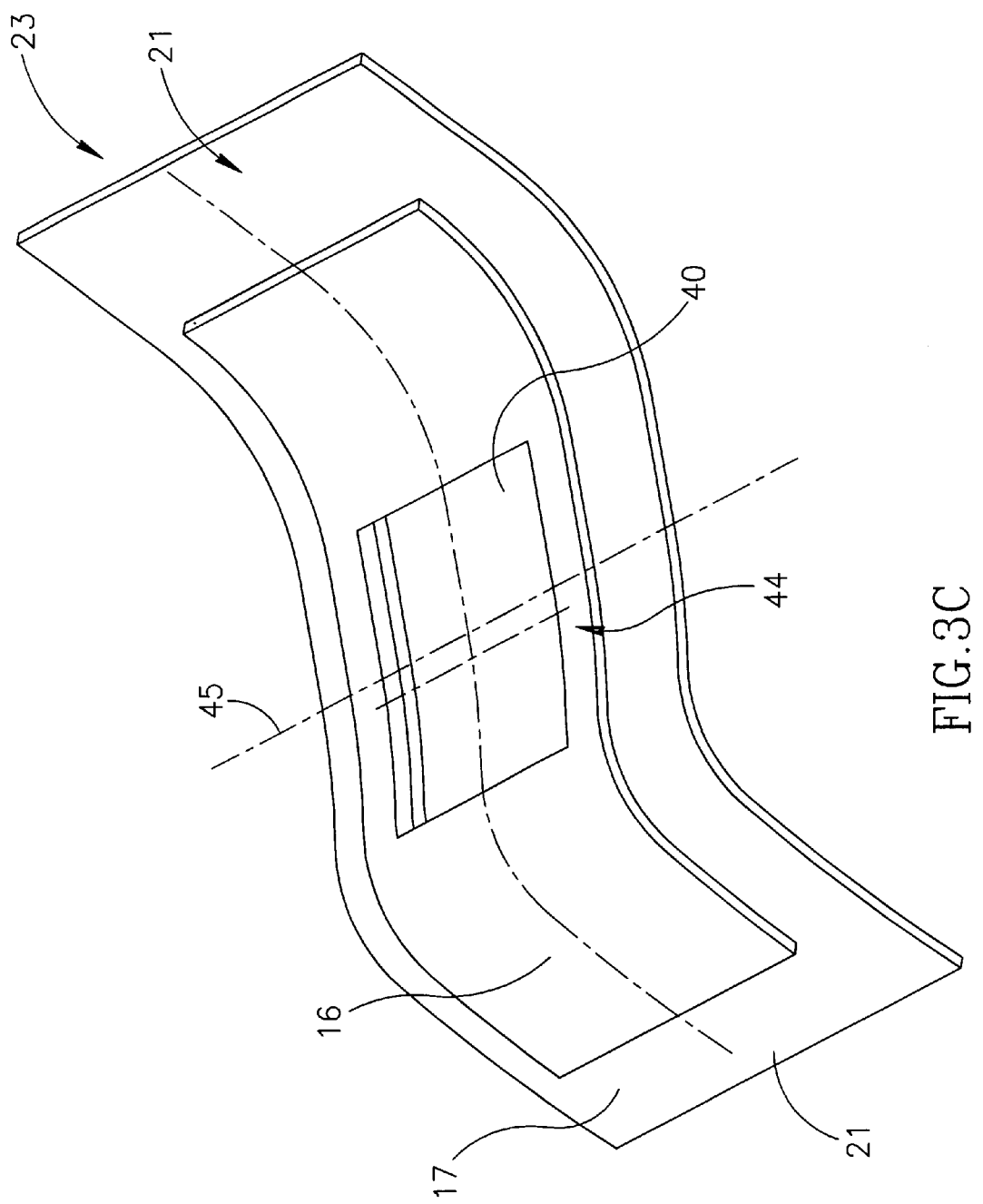

Reference is now made to FIGS. 3A–3C which illustrate the component parts of the scanning probe 27, including the transmitter 18, receiver 20, matching layer 22 and piezo-ceramic plate 16 with backing material 17.

FIG. 3A is a rear view of the scanning probe 27. Similar items to those in previous figures carry similar numerals and will not be described further. The piezo ceramic plate 16 has, for example, a square aperture 40 (other shapes of aperture may be utilized) cut into it, which is not symmetrical about the axis of symmetry 45 of the piezo-ceramic plate 16. The matching plate 22, which is glued with non sound-absorbent acoustic adhesive (or glue) to transmitter/receiver 25 as described hereinabove, is placed over the square aperture 40 on the front face (not shown) of the piezo-ceramic plate 16. The square aperture 40 has the effect of decoupling the transmitter 18/receiver 20 from the piezo-ceramic plate 16 in order to allow the transmitter 18 and receiver 20 to vibrate independently.

The transmitter/receiver 25 is in the form of a circular disc 42, which is, for example, made of plastic and is divided into two by a central portion 44. The circular disc 42 and matching layer 22 are formed as one unit. Piezo-ceramic material similar to that of the piezo-ceramic plate 16 forms the transmitter 18 and receiver 20, which are of half-disc form, are inserted into the circular disc to freely vibrate, and are divided by central portion 44. The transmitter 18 and receiver 20 are of thickness of 0.50 times the wavelength to be transmitted. The central portion 44 between the transmitter 18 and receiver 20 serves to decouple the transmitter 18 from the receiver 20 and is required to have a thickness of approximately 0.50 times the wavelength of the transmitted energy waves (frequency approx. 2.5 MHz, i.e., the natural frequency of transmitter/receiver as described hereinabove). Similar independent electrical contacts to those of the piezo-ceramic plate 16 suitably arranged for supplying an electric current to the transmitter 18 and receiver 20 are in place. The contact points are arranged to be on the opposite face of the transmitter 18 and receiver 20 to the face touching matching layer 22. Isolation of the transmitter 18 from the receiver 20 is ensured by the central portion 44 between them, as mentioned hereinabove. This ensures that the receiver 20 is free to vibrate upon receipt of energy waves 22 from the fetal heart 28 and does not disturb the transmitter 18 and visa versa. It should also be noted that the thickness of transmitter 18 and receiver 20 must be less than 0.5 times the wavelength of the natural frequency of vibration of piezo plate 16 when it is in the second harmonic of vibration.

As mentioned above, the aperture 40 is placed asymmetric to the axis of symmetry 45 of the piezo-ceramic plate 16. This means that the axis of symmetry 45 divides the aperture 40 into two unequal parts, as shown by arrows 47, 53. This creates an asymmetry of each half of the piezo-ceramic plate 16 created by the axis of symmetry 45. This is necessary so that when the piezo-ceramic plate 16 vibrates at its natural frequency of vibration of the second harmonic, the scanner 23 will vibrate in the second mode of vibration according to beam theory which gives high scanning frequencies for the input current frequencies described above. If the second mode of vibration were not used, the input current frequency would need to be very high to achieve the same scanning result. More importantly, this is the most efficient form of vibration for the scanner 23 as well as for the transmitter 18 and receiver 20 to be integrated and scan synchronously as transmitter 18 and receiver 20 fit into area 19a of representation 19 (FIG. 1).

FIG. 3B illustrates the transmitter/receiver 25 in place within the scanner 27. The direction of movement of the piezo-ceramic plate 16 in response to the applied alternating current is shown via the graphical representation at the top. Each half of the plate 16 (either side of the axis of symmetry 45) moves in an opposite direction to the other at any given moment in relation to the X and Z axis, as shown. This is further illustrated in FIG. 3C, which illustrates the vibrating plate 16 in this scenario.

It should be noted that if there were an asymmetry in the aperture 40 along, for example, another axis of symmetry 49 as shown in FIG. 3B, the second mode of vibration would also be exhibited in the Y-Z direction.

Figure 4A:
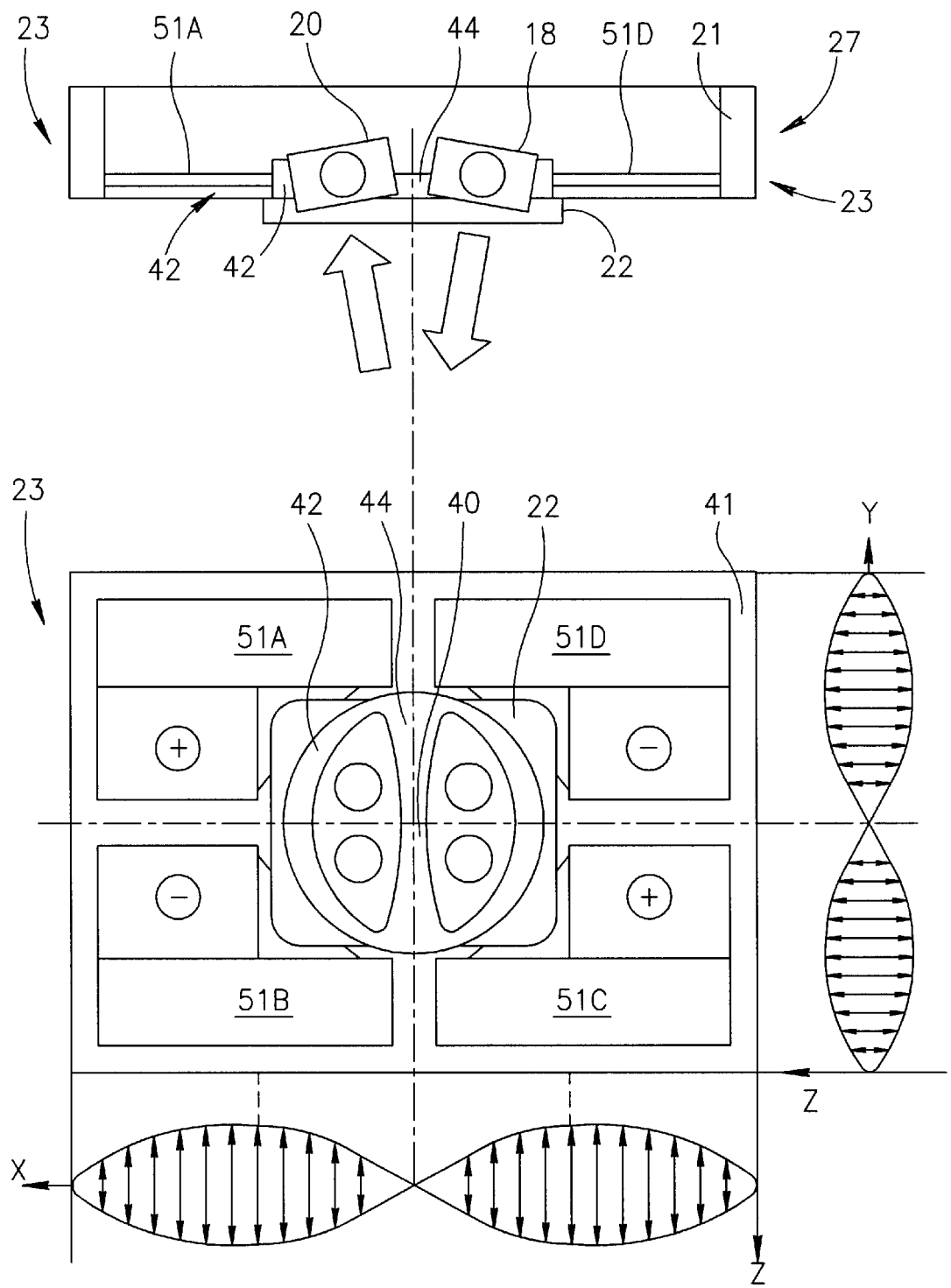
FIGS. 4A–4C illustrate the scanner. the scanning surface and the scanning results in a different orientation.
Figure 4B:
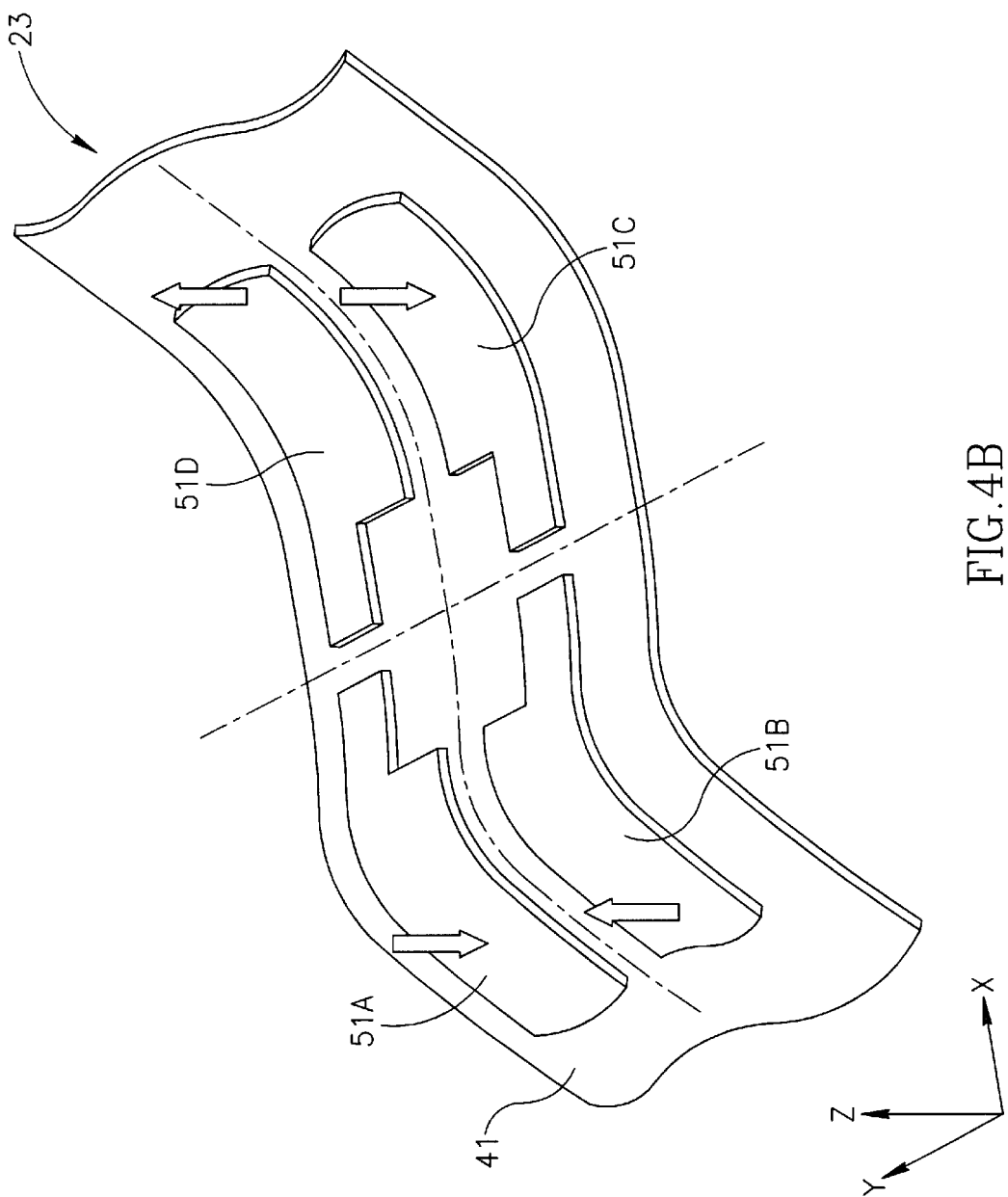
Figure 4C:
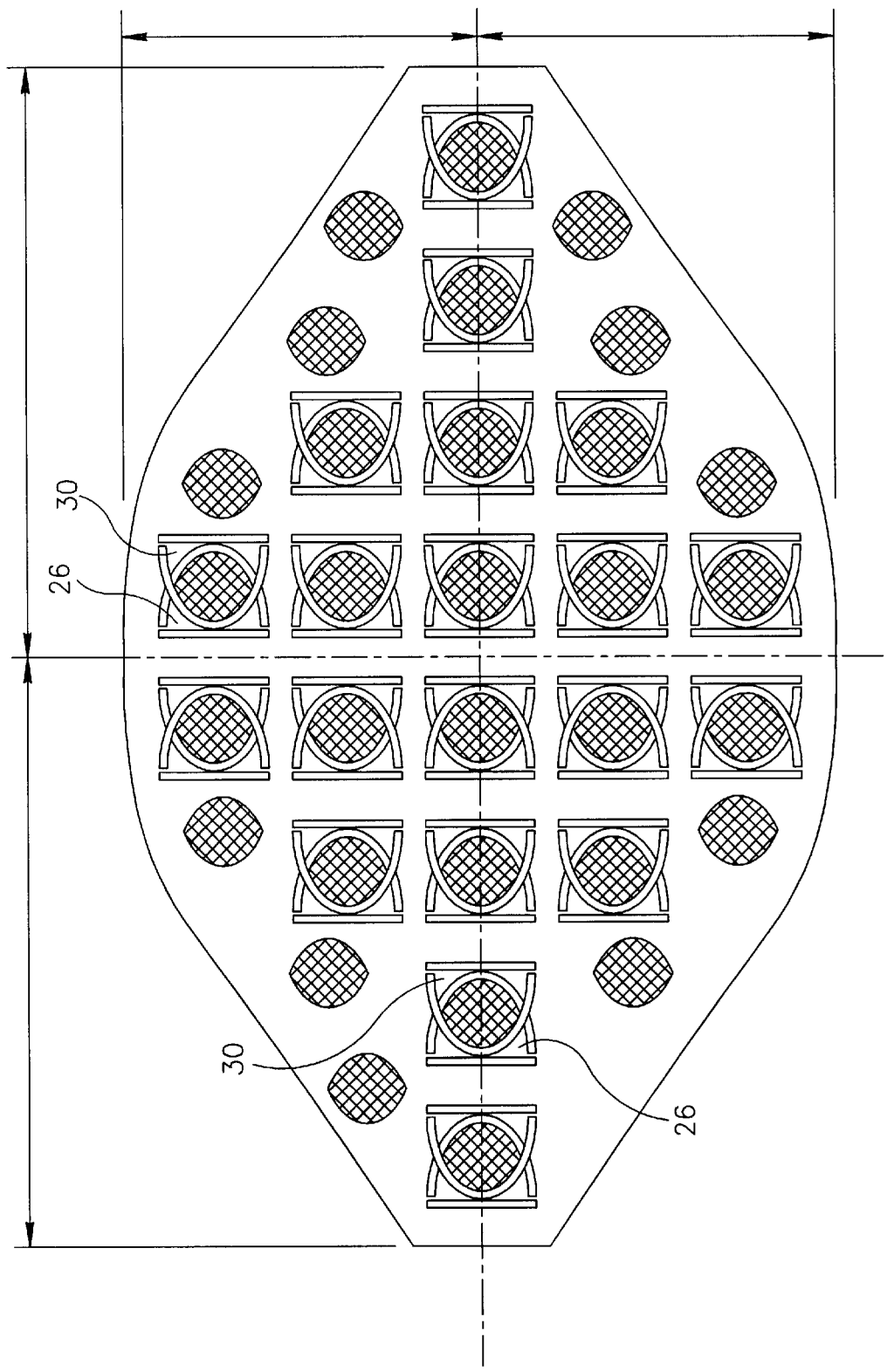

Reference is now made to FIGS. 4A–C. FIG. 4A illustrates a different orientation of piezo-ceramic material in relation to the scanner 23, to achieve a more flexible vibration of the scanner 23 and to achieve voltage variation of the scanning angle. FIG. 4B illustrates the scanning surface, and FIG. 4C illustrates the scanning result on the mother's body. Similar items to those in previous figures have similar reference numerals and will not be described further.

Piezo-ceramic sectors 51A–51D with electrodes 55A–55D are mounted on a backing case 41. Backing case material may be brass, for example, with a thickness of 50–200 micrometers. The purpose of the backing case material is to add strength to the piezo-ceramic disc sectors 51A–51D. Thus, the sectors 51A–51D can be as thick as 0.2 mm (approximately), which allows low voltages of approximately 2–15 V to be used to obtain the necessary vibrations. The backing case 41 is also covered with isolating material such as plastic, with a thickness of approximately 0.02 mm (not shown). The low voltage used decreases the chances of electric shock to the mother. The backing case 41 (typically plastic) is in the scanner 23. Aperture 40 is symmetrical to the X and Y axes.

Prior to the application of current to all four piezo-ceramic sectors 51A–51D, their polarities may be paired in a diagonal fashion as shown. Thus, two of the piezo-ceramic sectors 51A, 51C have a positive polarity and the other two piezo-ceramic sectors 51B, 51D have a negative polarity on their top surface. When current is applied, sectors 51 with the same polarity move together in response to the applied current. This causes the movements shown in the X-Z axis and the Y-Z axis as shown, which produces the movement of the scanner 23 without movement of the transmitter 18, receiver 20, matching layer 22 and circular disc 42. The exemplary scanning pattern obtained is shown in FIG. 4C with a + or −10 degree scanning angle (resulting in a total arc of 20 degrees scanned) obtained for the semi-circles of the transmitter 18 and receiver 20 as shown. Thus, there is a simultaneous second mode vibration in the X-Z and Y-Z directions.

As described hereinabove, this effect could be obtained by having asymmetries in the aperture 40 (FIG. 3B). It should be noted that different shapes of piezo-ceramic sectors 51 may be used, and that the effect of different polarities may be achieved by applying signals that differ in phase by 180 degrees. Each piezo-ceramic sector 51 may also be independently vibrated in order to achieve a more flexible scanning pattern.

The applied voltage may be varied in order to vary the scanning angle using a fixed frequency. Thus, scanning can be achieved at a variety of positive to negative angles, for example, +/−1–20 degrees. The mother or operator may thus vary the voltage using a voltage regulator to focus on an area containing the fetal heart 28.

Figure 5:
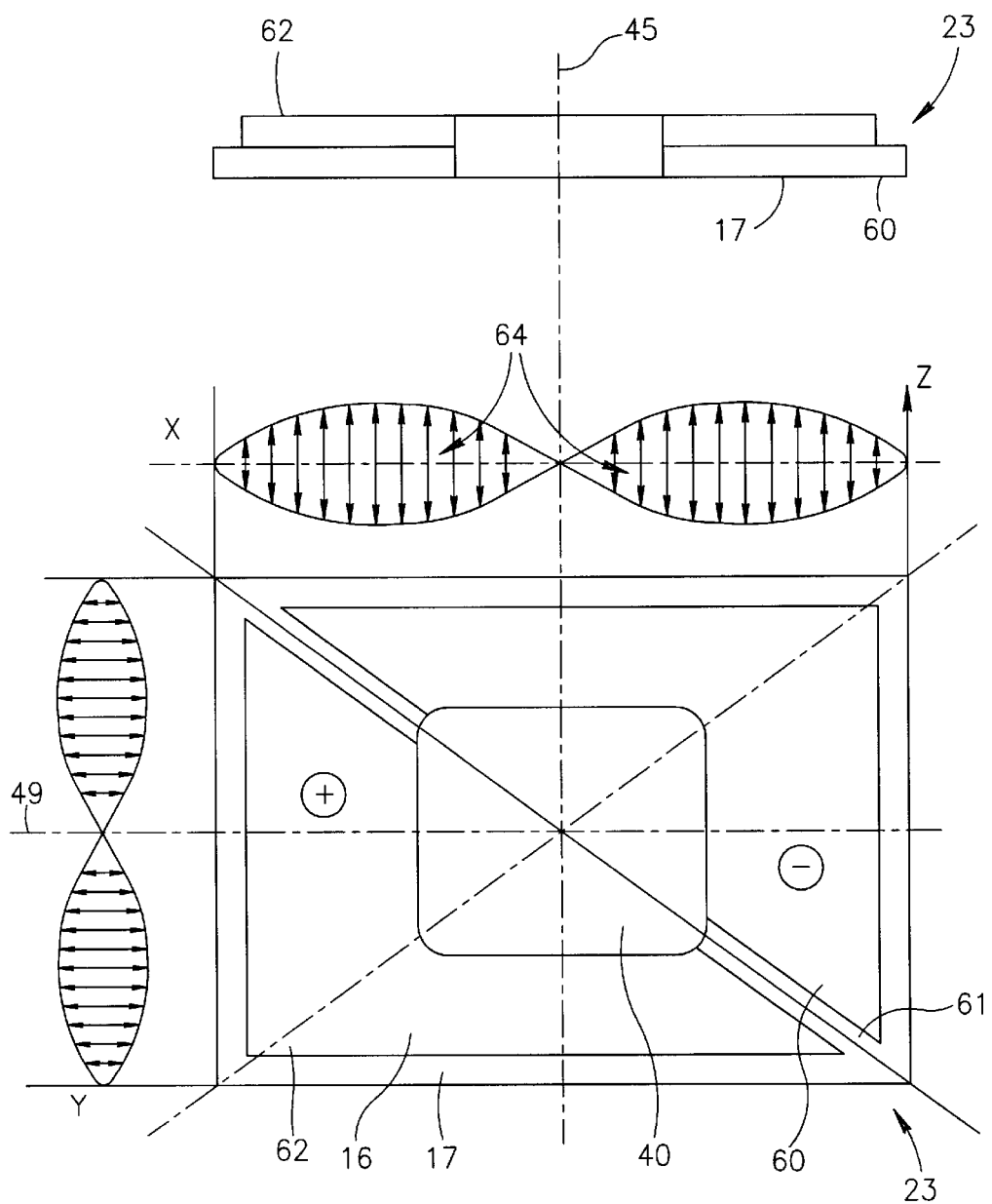
FIG. 5 illustrates another configuration of the scanner.

Reference is now made to FIG. 5 which illustrates another form of the scanner 23, where the piezo-ceramic plate 16 is divided into two unequal parts, (for example 60 and 62), along for example, a diagonal axis 61. Varying the applied frequency at a constant voltage can control the angle of scanning. This feature is especially useful for a small device where a voltage regulator is inappropriate. Similar items to those in previous figures have similar reference numerals and will not be described further.

The aperture 40 is symmetrical about the axis of symmetry 45 of the piezo-ceramic plate 16. The inequality of the two parts 60, 62 of the piezo-ceramic plate 16 causes the scanner 23 to vibrate in the second mode of vibration in the X-Z and Y-Z directions, which is beneficial for the reasons described above. The scanning pattern is achieved because there is asymmetry and consequential different natural frequencies of vibration about the axes of symmetry 45, 49 of the plate 16 (which is now divided diagonally). The orientations of scanning achieved by the configuration of FIG. 5 are shown graphically with reference to the X-Z and Y-Z axes. The frequency of the applied current may be varied by the user and by programmable algorithms with suitable hardware and/or software.

Figure 6A:
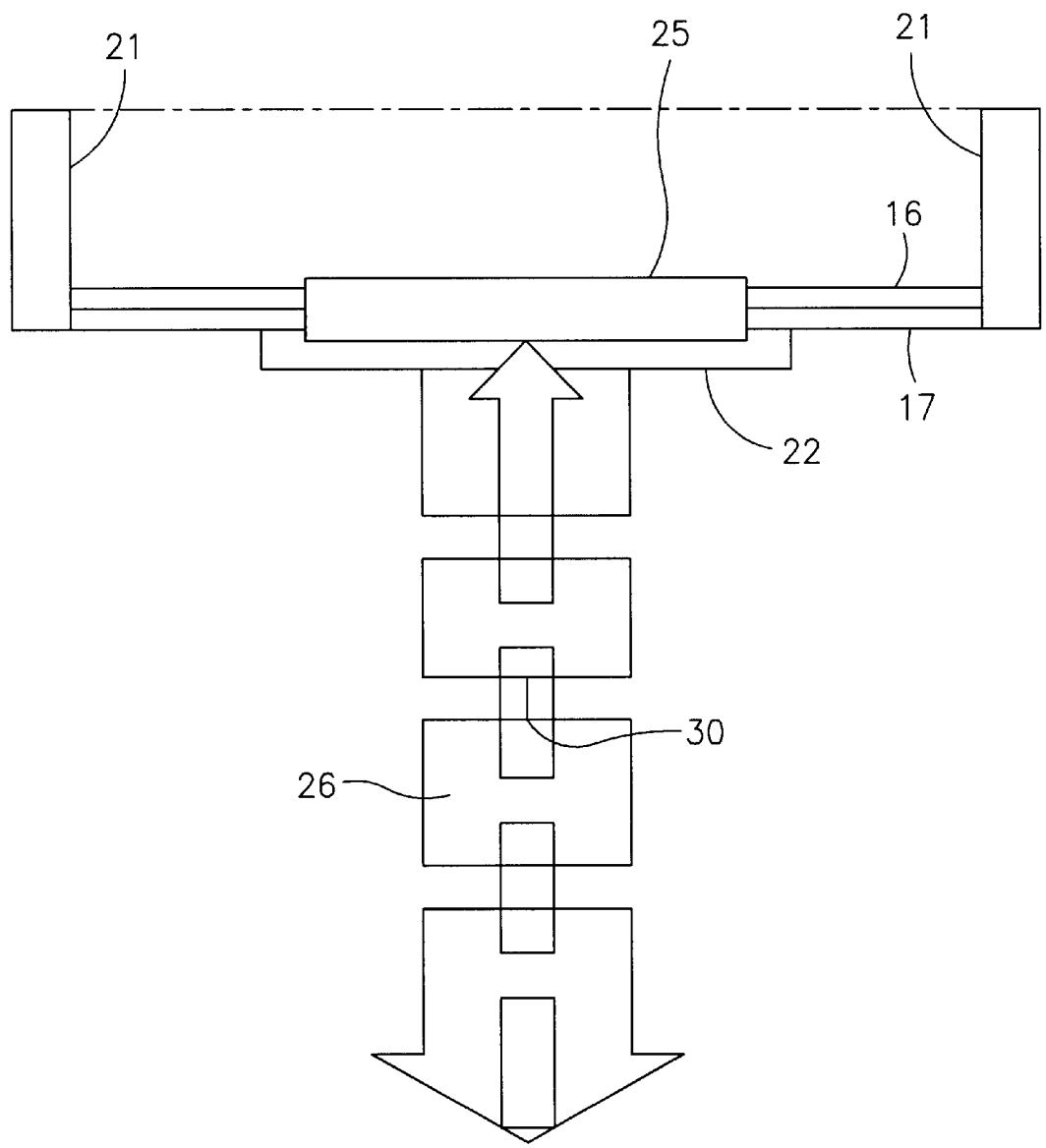
FIGS. 6A–6C illustrate the operation of the scanning system during pulsed-echo ultrasound mode.
Figure 6B:
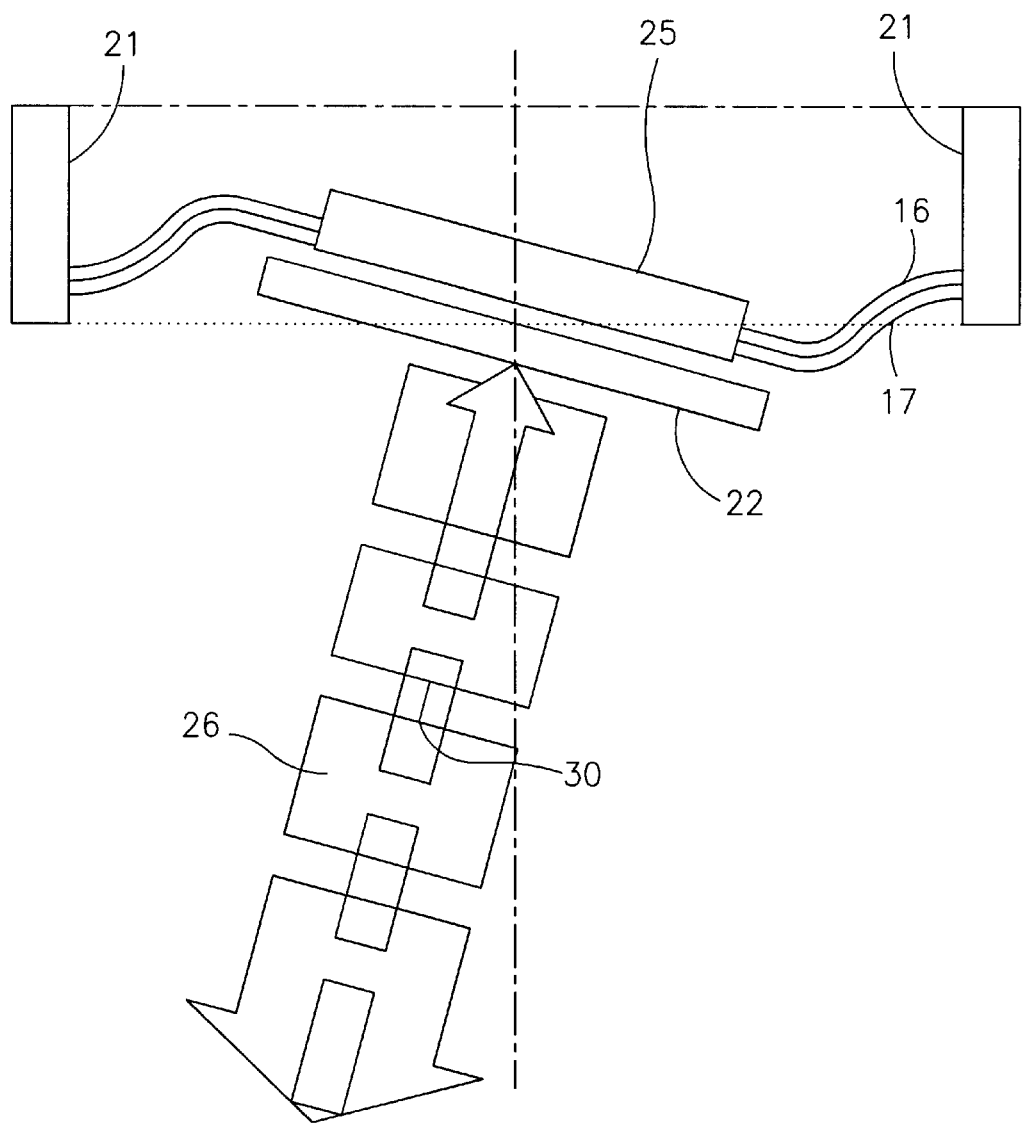
Figure 6C:
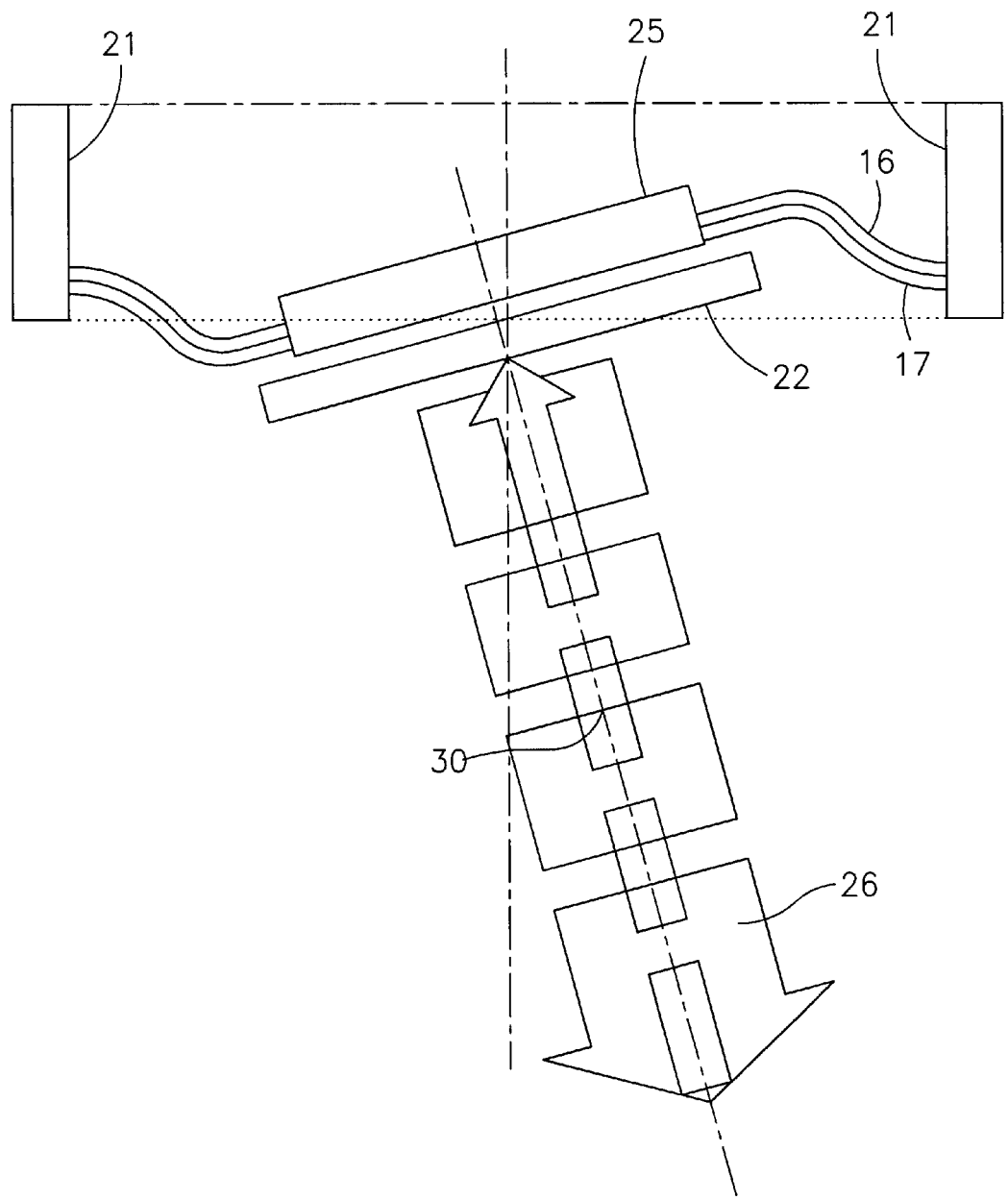
Figure 7A:
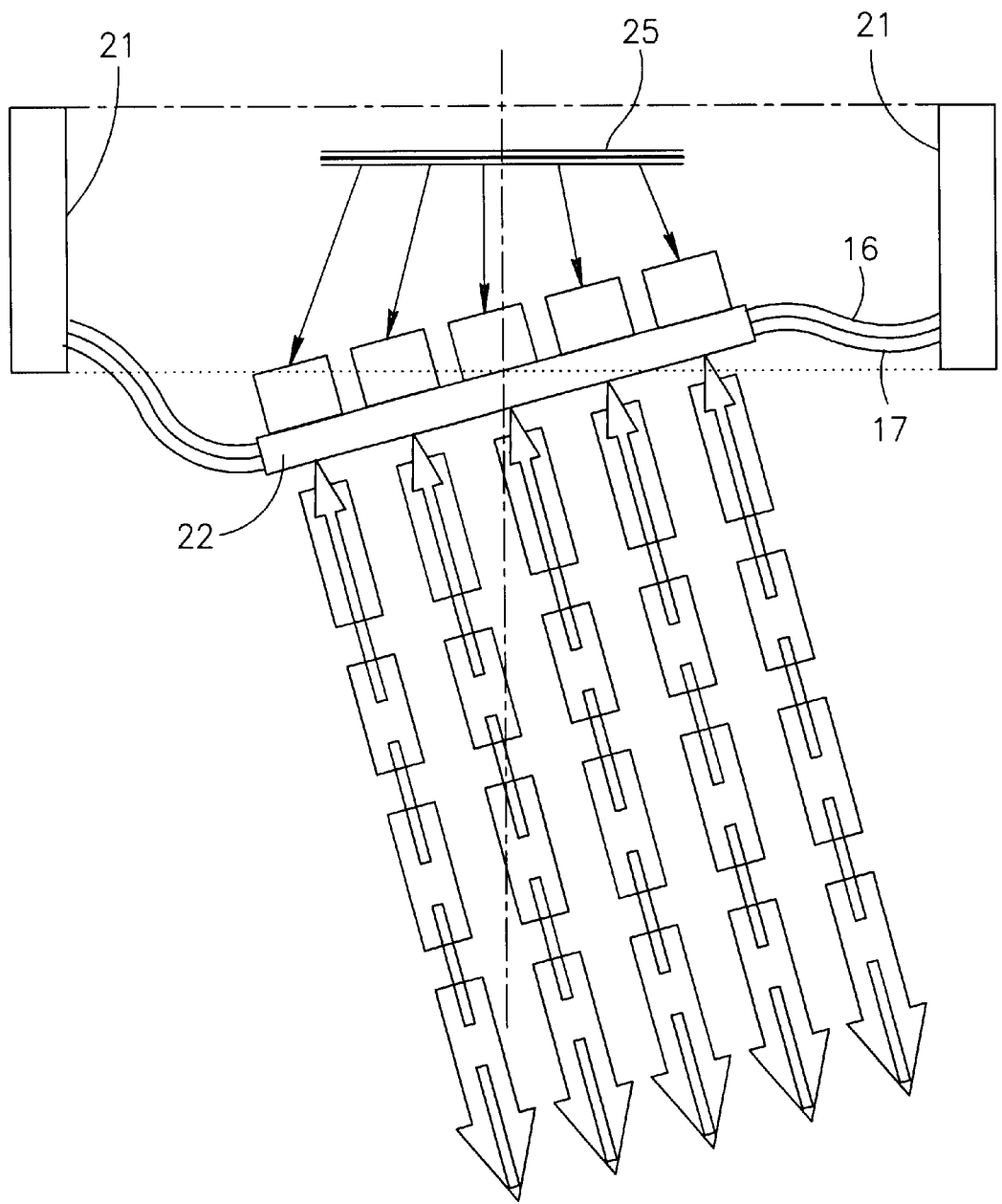
FIGS. 7A–7D illustrate a further embodiment of the scanning system, with an array transducer comprising multiple transmitter/receiver elements together.
Figure 7B:
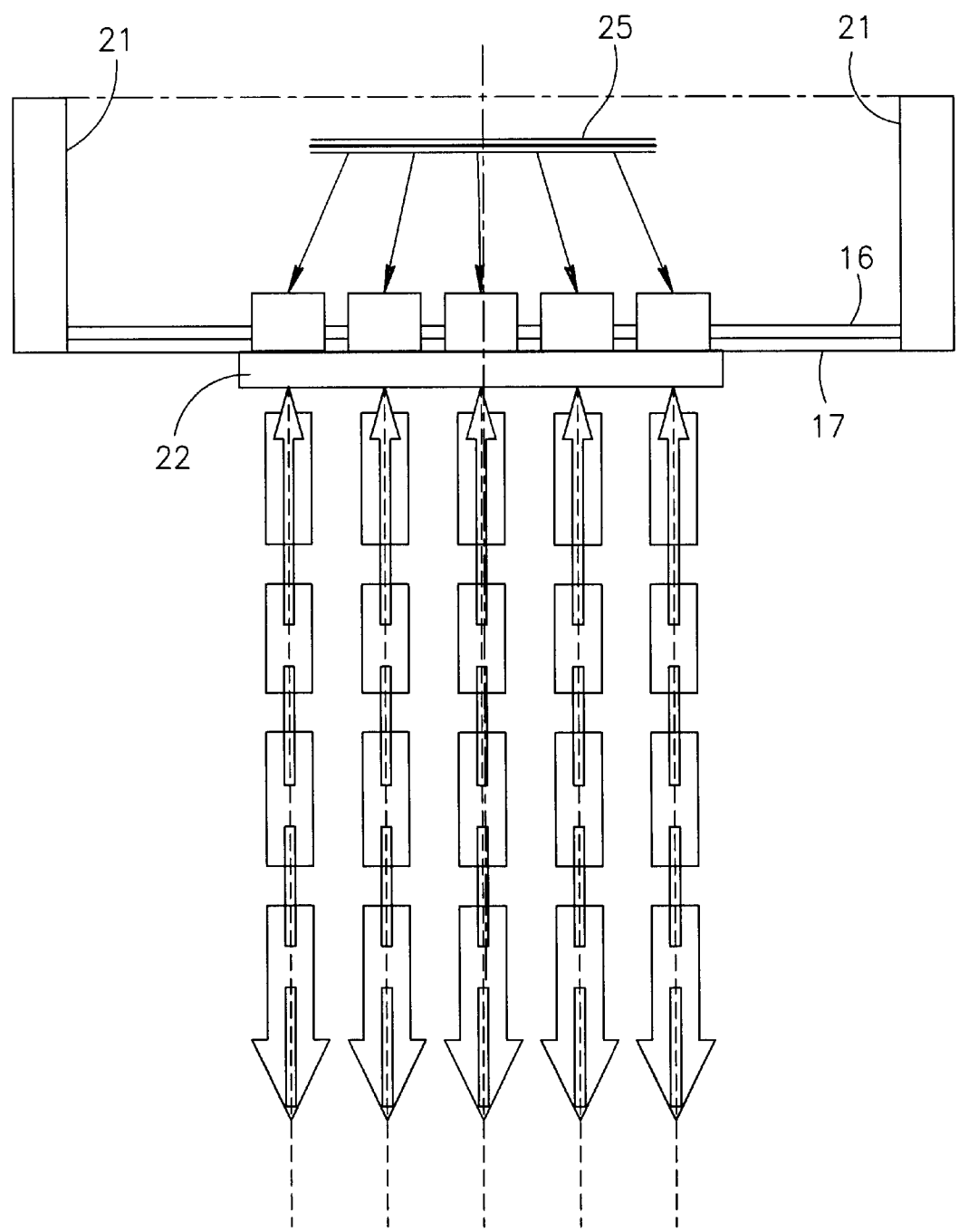
Figure 7C:
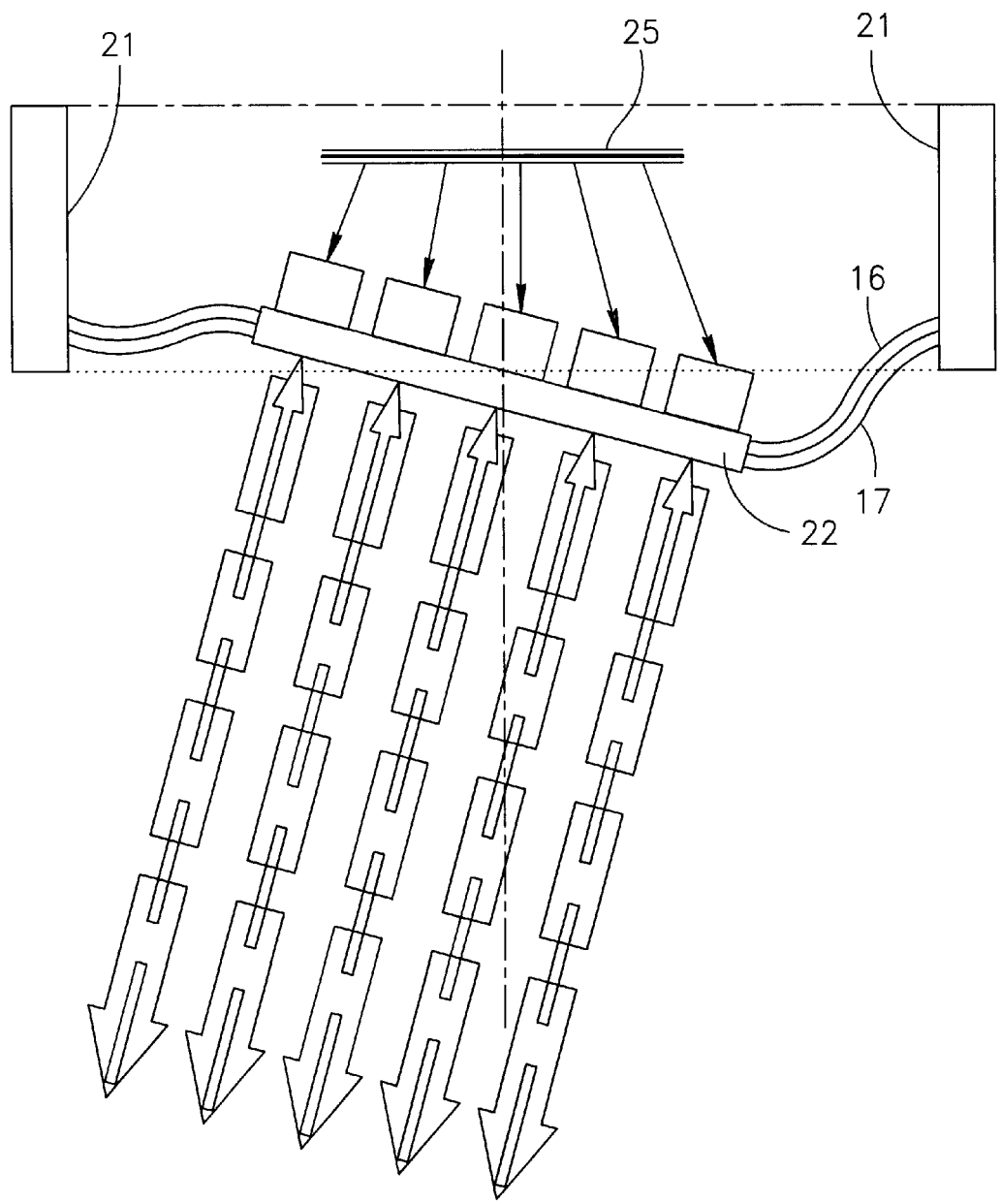
Figure 7D:
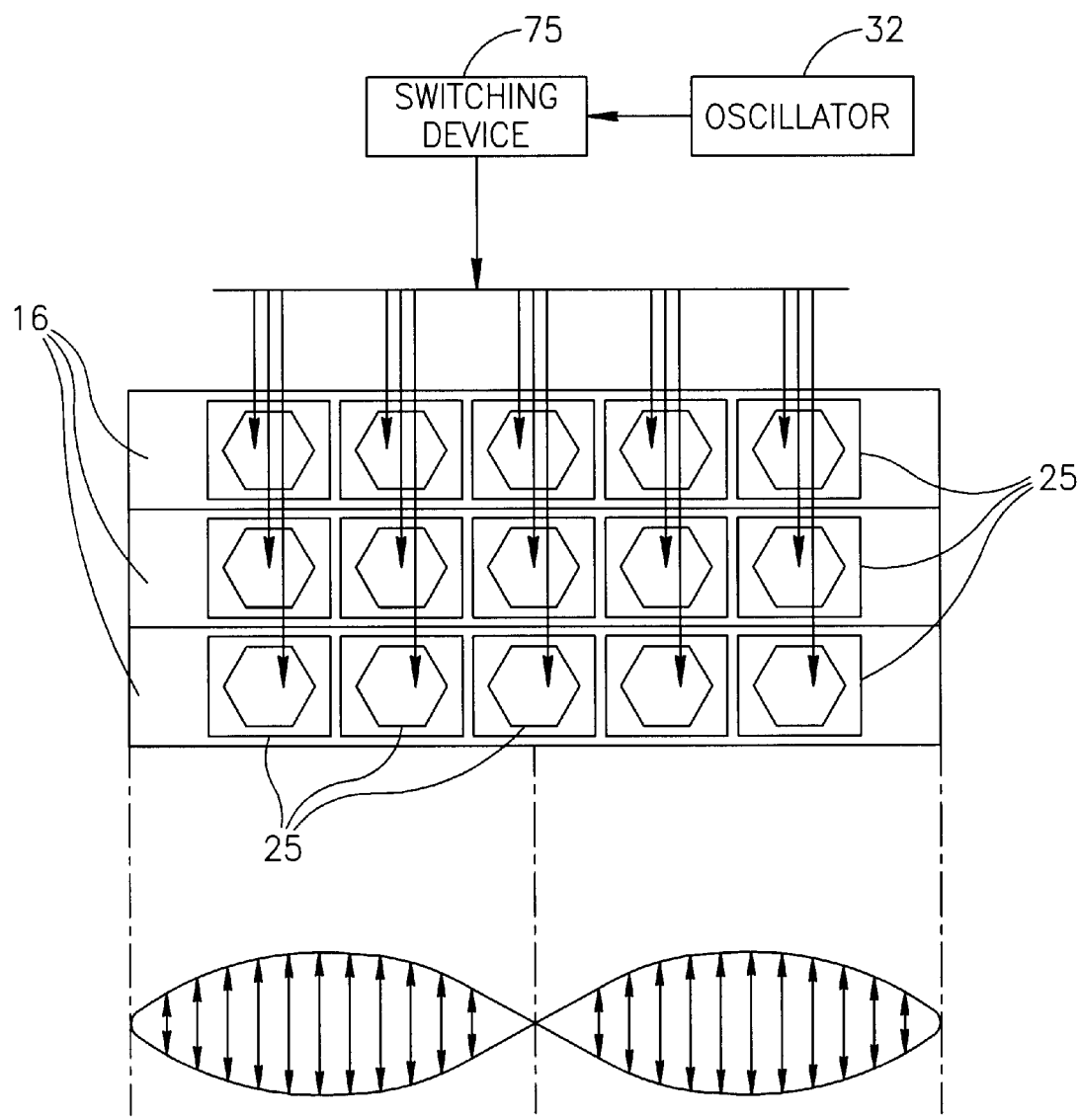

Reference is now made to FIGS. 6A, 6B and 6C, which are illustrations of the operation of the scanning system 12 when configured for pulsed-echo ultrasound mode of operation. Thus, the transmitter 18 and receiver 20 are typically a single unit, generally designated transmitter/receiver 25, as described hereinabove. In this unit, the transmitter/receiver 25 must transmit and wait to receive a returning wave as per the pulsed-echo ultrasuond technique of measuring shifts in wavelength due to motion. The pulsed frequency is 2–6 MHz, and the change in delay of receipt is proportional to the movement of the fetal heart 28. The transmitter/receiver 25 is one unit, configured to transmit and then later to receive using one piezo-ceramic element.

FIGS. 6A, 6B and 6C illustrate when the transmitter/receiver 25 is respectively oriented to scan to the zero angle position, when it is oriented to scan to the leftmost position and when it is oriented to scan to the rightmost position. Similar items to previous figures have similar numerals and will not be described further.

Scanning is achieved in a similar manner to that described hereinabove utilizing all the types of waves described hereinabove in relation to the first embodiment. Similar scanning angles along arcs of +/−20 degrees are achieved.

Figure 8A:
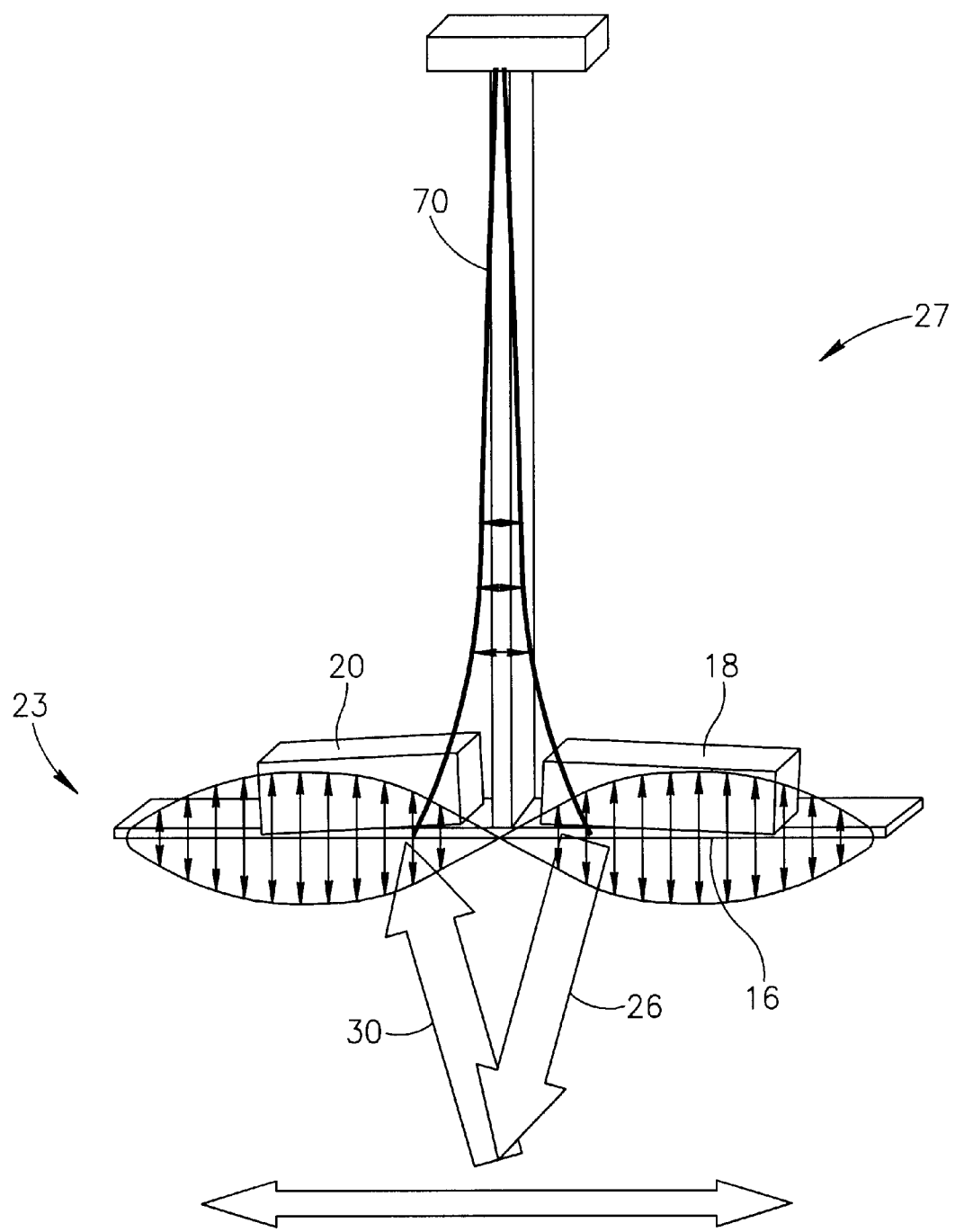
FIGS. 8A and 8B illustrate additional ways of scanning according to further embodiments of the invention.
Figure 8B:
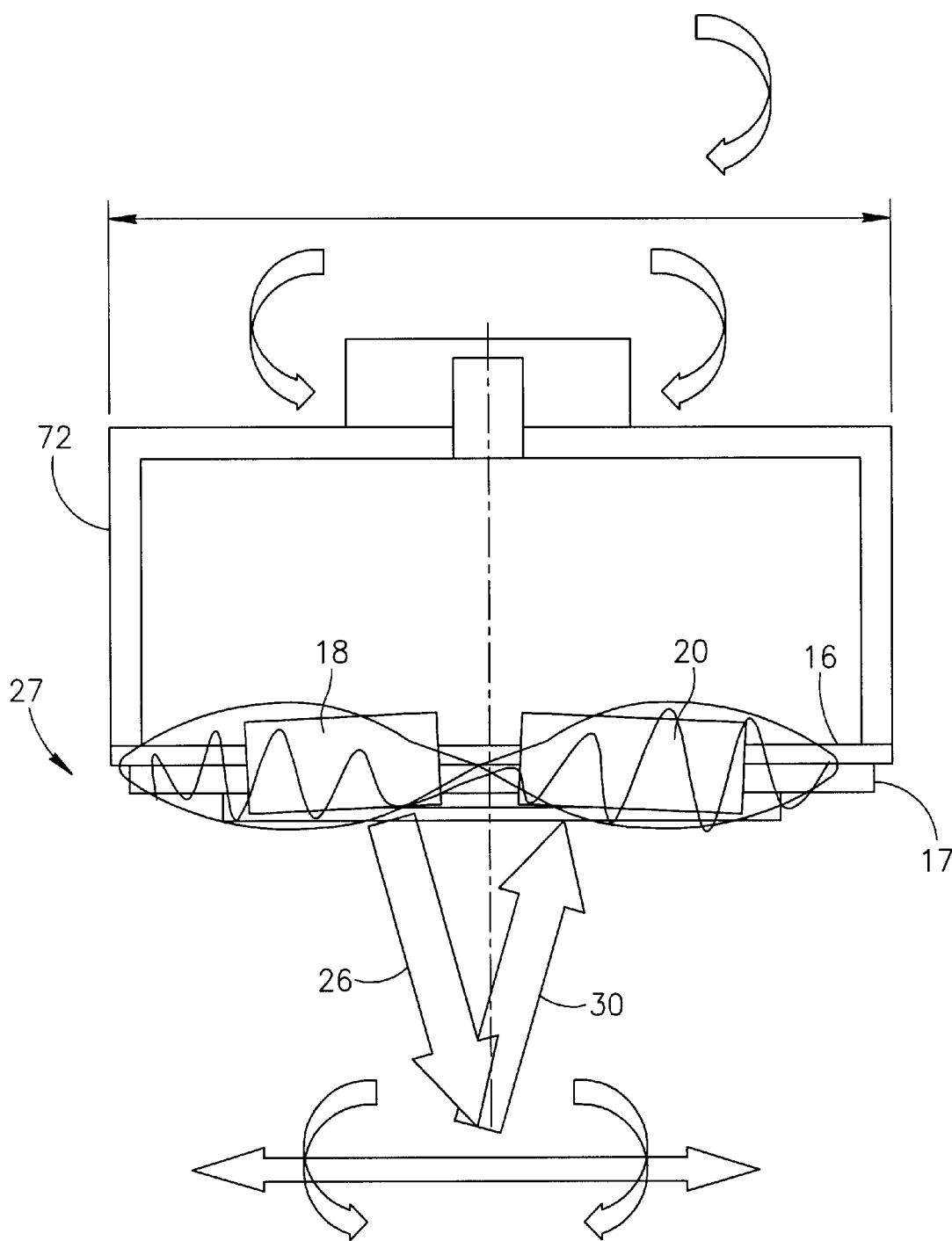

Reference is now made to FIGS. 7A–7D, which illustrate linear or curvilinear arrays of an ultrasound pulsed transducer. The scanning system 12 is made up of a number of unitary transmitter/receiver 25 elements in its rightmost, middle and leftmost scanning position, respectively. Similar items to those in previous figures have similar reference numerals and will not be described further. The arrangement shown enables a faster coverage of the area to be imaged as a large number of transmitter/receiver elements 25 are sweeping each point of the area to be imaged at a given moment. A switching device 75 may be used to select transmitter/receiver elements 25 to be used. Another advantage is that the area of imaging covered by the scanner 23 may be increased. Since a large number of transmitter/receiver elements 25 (in the order of hundreds) may be put into the flat section 19a of the mode of vibration representation 19 (FIG. 1), a very high resolution may be achieved using the pulsed-echo technique for precision ultrasound image applications. Reference is now made to FIG. 8A and FIG. 8B, which illustrate additional ways of scanning according to further embodiments of the present invention. Similar items to those in previous figures have similar reference numerals and will not be described further FIG. 8A shows a scanning probe 27 with two piezo-ceramic plates, the original piezo-ceramic plate 16, and a second piezo-ceramic plate 70. The first natural vibration mode of this plate occurs, for example, at a frequency of about 40 KHz and the second natural vibration mode of this plate occurs, for example, at a frequency of about 80 KHz. The second piezo-ceramic plate 70 is joined in a perpendicular fashion to the center of the first piezo-ceramic plate 16, and a sinusoidal current, for example, is applied to the second piezo-ceramic plate 70 in addition to that applied to the original piezo-ceramic plate 16. The combination of the two applied sinusoidal currents produces an increased deflection angle of scanning due to the additional side to side deflection of the piezo-ceramic plate 16. This is achieved without the need for an increase in applied frequency or voltage to the first piezo-ceramic plate 16 which would be required to achieve the same effect without the additional piezo-ceramic plate 70. Such an increase in frequency might be unpleasant to the user. Scanning angles of more than +/−20 degrees can be achieved in this way.

FIG. 8B illustrates how two circular motions can assist the scanning process. A torsional piezo-ceramic element 72 imparts a torsional motion in addition to the motion of the piezo-ceramic plate 16, which increases the scanning area of probe 27.

The input to the piezo-ceramic plate 16 is a sine or pulse wave, as described hereinabove, at a resonant frequency corresponding to the second mode of vibration of the piezo-ceramic plate, which may vary depending on the specific dimensions and materials used. This produces a standing wave, where all transmitter/receivers 25, are operating in the same direction.

Figure 9:
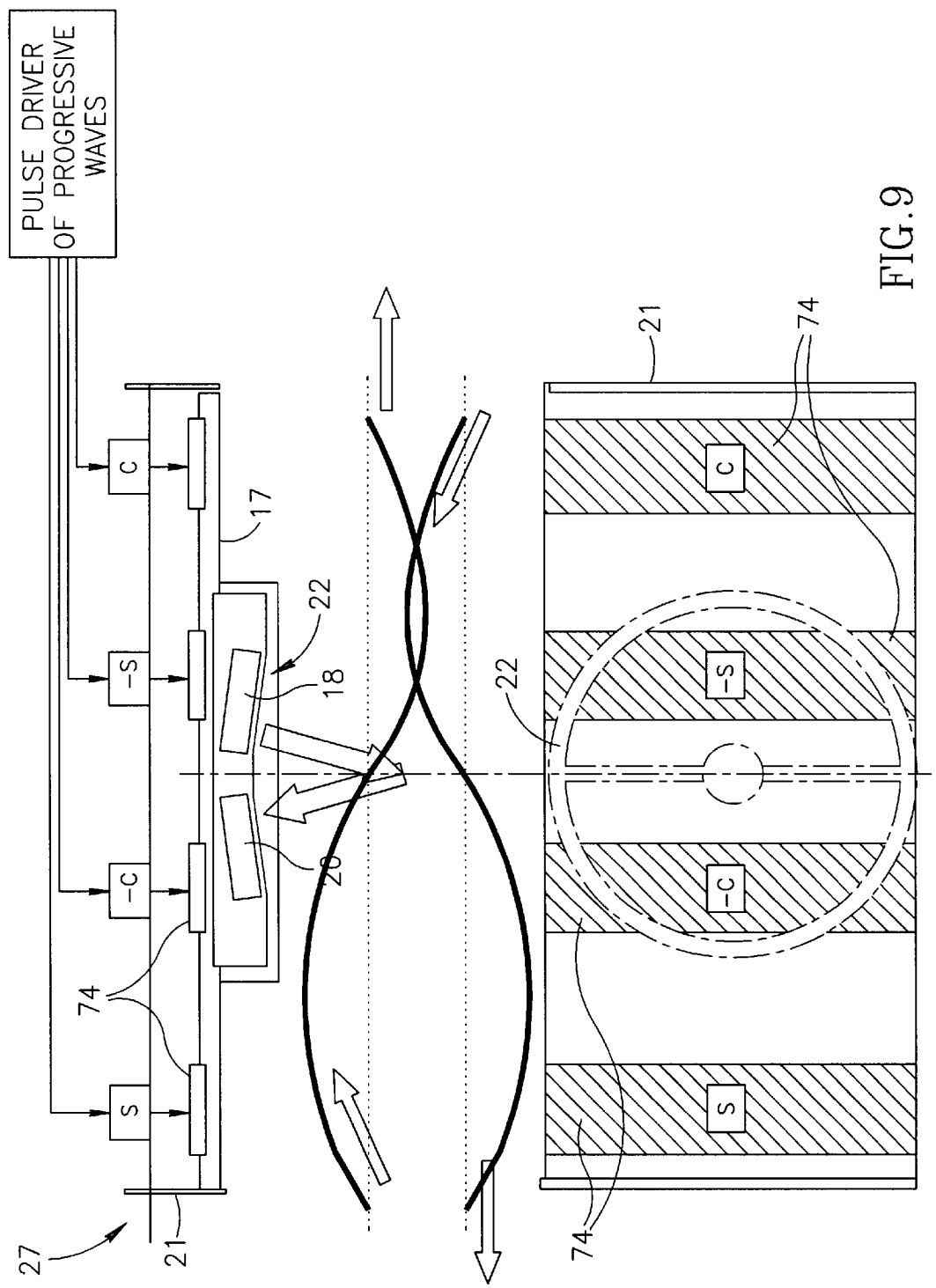
FIG. 9 illustrates additional ways of scanning using progressive scanning waves.

A scanning probe 27 with travelling-scanning waves is shown in FIG. 9. These waves are progressive, in that they are formed by an accumulation of wave inputs. For example, backing plate 17 may be divided into piezo-ceramic sections 74 to which sine and cosine electrical signals are applied. This generates a progressive wave to the right and the left in the plate 17. The matching layer 22 of the transmitter 18 and receiver 20 moves in same direction as the progressive wave of the plate 17.

When using progressive waves, the frequency of scanning depends on geometrical parameters of the piezo-ceramic sections 74 rather than on the length of the plate as is the case with standing waves, This method allows for simplified construction and reduced dimensions, while at the same time increasing the diagnostic area and scanning resolution.

In general, gel is used in conjunction with ultrasound to prevent air pockets between the skin and ultrasonic probe from changing transmitted and received frequencies, that is, to prevent energy loss. If a very high frequency of scanning vibration is used in conjunction with the present invention, air pockets are expelled preventing the need for gel.

The device described hereinabove is, of course, not limited to the use of fetal heart monitoring but has many other applications where a lightweight, mechanically uncomplicated scanning system is required which is oscillating in its characteristic frequency. For example, the system can be used for vascular applications at a transmitter/receiver (transducer) frequency of 4–10 MHz with similar scanner frequency and also for other medical diagnostic applications. This may be with or without attendant transmission and receipt of energy waves. The frequency of the piezoelement's vibrations depends on a number of factors which include geometrical parameters and shape as described herein, the number of electrodes on the piezoelement and the attachment points of the piezoelement to the fixed structure.

While preferred embodiments of the present invention have been described, so as to enable one of skill in the art to practice the present invention the preceding description is intended to be exemplary only. It should not be used to limit the scope of the invention, which should be determined by reference to the following claims.

What is claimed is:

1. Apparatus for transmitting and receiving energy waver comprising:
   at least one piezoceramic scanner in communication with a first oscillator;
   at least one piezoceramic transmitter in communication with a second oscillator and operatively coupled to said piezoceramic scanner; and
   at least one piezoceramic receiver operatively coupled to said piezoceramic scanner, wherein said piezoceramic transmitter is configure to transmit waves to an object, said receiver is configured to receive signals from said object, and said piezoceramic scanner is configured to vibrate so as to provide a wide scanning area of said object.

2. The apparatus of claim 1 wherein said first oscillator and said second oscillator are configured for operation based on a sinusoidal wave input.

3. The apparatus of claim 1 wherein said first oscillator and said second oscillator are configured for operation based on a standing wave input.

4. The apparatus of claim 1 wherein said scanner is a piezoceramic plate.

5. The apparatus of claim 1 wherein said scanner is a piezoceramic disc.

6. The apparatus of claim 1 wherein said scanner includes a piezoceramic torsional element.

7. The apparatus of claim 1 wherein said scanner, said transmitter and said receiver are coupled so as to oscillate simultaneously.

8. The apparatus of claim 1 wherein said scanner, said transmitter and said receiver are coupled so as to oscillate simultaneously at a second mode of oscillation.

9. The apparatus of claim 1 wherein said at least one piezoceramic trasmitter and at least one piezoceramic receiver are configured in various shapes to achieve variability in scanning.

10. The apparatus of claim 1 wherein said at least one piezoceramic transmitter and said at least one piezoceramic receiver are configured to transmit and receive waves in a perpendicular direction with respect to said scanner.

11. The apparatus of claim 1 additionally comprising a filter layer operatively coupled to said scanner.

12. The apparatus of claim 11 wherein said filter layer has a thickness of approximately ¼ the wavelength of said energy waves transmitted by said at least one piezoceramic transmitter.

13. The apparatus of claim 1 wherein said at least one piezoceramic transmitter includes multiple piezoceramic transmitter elements.

14. The apparatus of claim 1 wherein said at least one piezoceramic receiver includes multiple piezoceramic receiver elements.

15. A system for detecting a fetal heartbeat comprising:
   at least one piezoceramic transmitter;
   at least one piezoceramic receiver;
   at least one piezoceramic scanner operatively coupled, to said at least one piezoceramic transmitter and said at least one piezoceramic receiver;
   a processor in communication with said scanner, said transmitter and said receiver, wherein said processor comprises a first oscillator in communication with said scanner and a second oscillator in communication with said transmitter wherein said first oscillator is configured to vibrate said piezoceramic scanner and said second oscillator is configured to transmit waves to said object; and
   an amplifier unit in communication with said piezoceramic receiver, said amplifier unit configured for converting said received waves into an output signal.

16. The system of claim 15 wherein said first oscillator and said second oscillator are configured for operation based on a sinusoidal wave input.

17. The system of claim 15 wherein said first oscillator and said second oscillator are configured for operation based on a standing wave input.

18. The system of claim 15 wherein said at least one scanner includes a piezoceramic disc.

19. The system of claim 15 wherein said at least one scanner includes a piezoceramic plate.

20. The system of claim 15, wherein said at least one scanner includes a piesoceramic torsional element.

21. The system of claim 15 wherein said at least one piezoceramic transmitter and said at least one piezoceramic receiver are configured in various shapes to achieve variability in scanning.

22. The apparatus of claim 15 wherein said scanner, said transmitter and said receiver are coupled so as to oscillate simultaneously.

23. The apparatus of claim 15 wherein said scanner, said transmitter and said receiver are coupled so as to oscillate simultaneously in a second mode of oscillation.

24. The system of claim 15 wherein said output signal is in the form of audio output via speaker.

25. The system of claim 15 wherein said output signal is in the form of digital display via counter.

26. The system of claim 15 wherein said at least one piezoceramic transmitter and said at least one piezoceramic receiver are configured to transmit and receive waves in a perpendicular direction with respect to said scanner.

27. The system of claim 15 additionally comprising a filter layer operatively coupled to said scanner.

28. The system of claim 27 wherein said filter layer has a thickness of approximately ¼ the wavelength of said energy waves transmitted by said at least one piezoceramic transmitter.

29. The system of claim 15 wherein said at least one piezoceramic transmitter includes multiple piezoceramic transmitter elements.

30. The system of claim 15 wherein said at least one piezoceramic receiver includes multiple piezoceramic receiver elements.

31. A method for detecting a fetal heartbeat comprising the steps of:

provide at least one piezoceramic transmitter, at least one piezoceramic receiver, and at least one piezoceramic scanner operatively coupled to said at least one piezoceramic transmitter and said at least one piezoceramic receiver;

energizing said scanner by a first oscillator, simultaneously energizing said piezoceramic transmit by a second oscillator so as to create a scanning range over a predetermined while transmitting mechanical waves; and receiving signals over said predetermined arc, said signals corresponding to a fetal heartbeat.

32. The method of claim 31 additionally comprising the step of varying the scanning sequence.

33. The method of claim 32 wherein the step of varying he scanning sequence is accomplished by varying a voltage input.

34. The method of claim 32 wherein the step of varying the scanning sequence is accomplished by varying frequency input.

35. The method of claim 32 wherein the step of varying the scanning sequence is accomplished by varying a wave input.

36. The method of claim 31 wherein the step of energizing includes inputting a continuous signal.

37. The method of claim 31 wherein the step of energizing includes inputting a pulsed signal.

38. The method of claim 31 wherein the step of energizing includes inputting several signals for progressive wave scanning.

39. A piezoceramic scanner coupled to a transmitter and a receiver and in communication with a first oscillator wherein said first oscillator is configured to transmit electrical waves to said piezoceramic scanner, and wherein said electrical waves are transformed into mechanical waves within said piezoceramic scanner, said mechanical waves configured to vibrate said piezoceramic scanner.

* * * * *